(12) United States Patent
Wakabayashi et al.

(10) Patent No.: US 12,030,997 B2
(45) Date of Patent: Jul. 9, 2024

(54) METHOD FOR PRODUCING WATER-ABSORBENT RESIN PARTICLES

(71) Applicant: NIPPON SHOKUBAI CO., LTD., Osaka (JP)

(72) Inventors: Ryota Wakabayashi, Himeji (JP); Shin-ichi Fujino, Himeji (JP); Mai Sato, Himeji (JP); Yoshihiro Shobo, Himeji (JP); Shin-ya Katsube, Himeji (JP); Kunihiko Ishizaki, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 847 days.

(21) Appl. No.: 17/055,249

(22) PCT Filed: May 15, 2019

(86) PCT No.: PCT/JP2019/019225
§ 371 (c)(1),
(2) Date: Nov. 13, 2020

(87) PCT Pub. No.: WO2019/221154
PCT Pub. Date: Nov. 21, 2019

(65) Prior Publication Data
US 2021/0269606 A1 Sep. 2, 2021

(30) Foreign Application Priority Data
May 16, 2018 (JP) .................. 2018-094742

(51) Int. Cl.
*C08J 3/24* (2006.01)
*A61F 13/53* (2006.01)
(Continued)

(52) U.S. Cl.
CPC ............... *C08J 3/245* (2013.01); *A61F 13/53* (2013.01); *B01J 20/267* (2013.01);
(Continued)

(58) Field of Classification Search
CPC ... C08J 3/245; C08J 3/12; C08J 233/02; C08J 2451/08; A61F 13/53; A61F 2013/530569;
(Continued)

(56) References Cited

U.S. PATENT DOCUMENTS

| 3,819,323 A | 6/1974 | Hemsath et al. |
| 7,265,190 B2 | 9/2007 | Dairoku et al. |
| 7,638,570 B2 | 12/2009 | Torii et al. |
| 2007/0149760 A1 | 6/2007 | Kadonaga et al. |

(Continued)

FOREIGN PATENT DOCUMENTS

| EP | 2 669 318 A1 | 12/2013 |
| JP | S63-14076 A | 1/1988 |

(Continued)

OTHER PUBLICATIONS

International Search Report dated Jul. 16, 2019, which issued in the corresponding PCT Patent Application No. PCT/JP2019/019225.

*Primary Examiner* — Ling Siu Choi
*Assistant Examiner* — Ronald Grinsted
(74) *Attorney, Agent, or Firm* — Dickinson Wright PLLC

(57) ABSTRACT

A production method includes a surface-crosslinking step of heating a mixture of a surface-crosslinking agent and a particulate dried polymer obtained with an acid group-containing unsaturated monomer as a main component. A moisture content of the particulate dried polymer is not greater than 15% by mass. A heating device including a rotary container and a plurality of heating tubes that are located within the rotary container, extend in an axial direction of the rotary container, and rotate together with the rotary container, is used in the surface-crosslinking step. The heating device includes a means for introducing and discharging a gas into and from the rotary container.

23 Claims, 7 Drawing Sheets

(51) Int. Cl.
  *B01J 20/26* (2006.01)
  *B01J 20/28* (2006.01)
  *B01J 20/30* (2006.01)
  *C08F 20/06* (2006.01)
  *C08J 3/12* (2006.01)
  *F26B 17/32* (2006.01)

(52) U.S. Cl.
  CPC ... *B01J 20/28004* (2013.01); *B01J 20/28016* (2013.01); *B01J 20/3021* (2013.01); *B01J 20/3078* (2013.01); *C08F 20/06* (2013.01); *C08J 3/12* (2013.01); *F26B 17/32* (2013.01); *A61F 2013/530569* (2013.01); *A61F 2013/530591* (2013.01); *C08J 2333/02* (2013.01); *C08J 2451/08* (2013.01)

(58) Field of Classification Search
  CPC ......... A61F 2013/530591; B01J 20/267; B01J 20/28004; B01J 20/3021; B01J 20/3078; C08F 20/06; F26B 17/32
  USPC .......................................................... 502/402
  See application file for complete search history.

(56) References Cited

U.S. PATENT DOCUMENTS

| | | | |
|---|---|---|---|
| 2016/0083533 A1* | 3/2016 | Imura | C08J 3/245 |
| | | | 525/329.7 |
| 2017/0014801 A1 | 1/2017 | Ikeuchi et al. | |
| 2017/0089640 A1* | 3/2017 | Nakata | F26B 3/22 |
| 2019/0201868 A1 | 7/2019 | Wakabayashi et al. | |
| 2019/0329219 A1 | 10/2019 | Watabe et al. | |
| 2019/0329220 A1 | 10/2019 | Watabe et al. | |

FOREIGN PATENT DOCUMENTS

| | | |
|---|---|---|
| JP | 2004-352941 A | 12/2004 |
| JP | 2008-038128 A | 2/2008 |
| JP | 2012012482 A | 1/2012 |
| JP | 2015-200499 A | 11/2015 |
| JP | 5918864 B2 | 5/2016 |
| WO | 88/07589 A1 | 10/1988 |
| WO | 2013/110415 A1 | 8/2013 |
| WO | 2014/181859 A1 | 11/2014 |
| WO | 2015/129917 A1 | 9/2015 |
| WO | 2017221911 A1 | 12/2017 |
| WO | 2018/092863 A1 | 5/2018 |
| WO | 2018/092864 A1 | 5/2018 |

* cited by examiner

METHOD FOR PRODUCING WATER-ABSORBENT RESIN PARTICLES

TECHNICAL FIELD

The present invention relates to methods for producing water-absorbent resin particles. Specifically, the present invention relates to methods, for producing water-absorbent resin particles, including a surface-crosslinking step.

BACKGROUND ART

A water-absorbent resin (SAP/Super Absorbent Polymer) is a water-swellable and water-insoluble polymer gelling agent, and is frequently used in various fields of absorbent articles such as disposable diapers and sanitary napkins, water retention agents for agricultural and horticultural use, water stopping materials for industrial use, and the like.

For the water-absorbent resin, various monomers and hydrophilic polymers are used as the raw materials thereof, and the most industrially produced is, from the viewpoint of fluid retention performance, a polyacrylic acid (salt)-based water-absorbent resin in which acrylic acid and/or a salt thereof is used.

With improvement of performance of disposable diapers, which are a main application of the water-absorbent resin, the water-absorbent resin is required to have various functions (improved physical properties). Specifically, the water-absorbent resin is required to have various physical properties such as gel strength, water-soluble content, moisture content, water absorption speed, liquid permeability, particle size distribution, urine resistance, antibacterial property, damage resistance, powder fluidity, deodorization property, anti-coloring property, low dust, and low residual monomer, as well as water absorption capacity under no load and water absorption capacity under load which are basic physical properties. In particular, in application to sanitary articles such as disposable diapers and the like, further improvement in water absorption speed is desired as a product becomes thinner.

Such a water-absorbent resin can be made into various forms such as sheet form, fiber form, film form, and the like, but are generally often made into powder form or particle form. Regarding a water-absorbent resin in powder form or particle form, it is known that the fluid retention performance, the handleability, and the feeling in use vary depending on the particle diameter, the particle size distribution, or the like thereof. Thus, a water-absorbent resin in powder form or particle form which has an appropriately controlled particle diameter or particle size distribution is desired. In particular, in application to sanitary articles such as disposable diapers and the like, from the viewpoint of water absorption capacity under load and liquid permeability, water-absorbent resin particles including a small amount of fine powder (fine particles having a particle diameter of less than 100 µm or less than 150 µm, particularly, fine particles having a particle diameter of less than 150 µm) are considered preferable. In addition, the water-absorbent resin particles are generally subjected to surface-crosslinking treatment in order to improve water absorption capacity under load and other absorption characteristics.

Examples of a main method for producing the water-absorbent resin in powder form or particle form include an aqueous solution polymerization method and a reverse phase suspension polymerization method. For example, in the case of the aqueous solution polymerization method, as illustrated in FIG. 7, normally, in order to finally obtain a water-absorbent resin in particle form, the method includes a polymerization step of performing aqueous solution polymerization of a water-soluble ethylenic unsaturated monomer, a gel-crushing (fine granulation) step of grinding a crosslinked hydrogel polymer obtained through the polymerization, a drying step of drying the ground gel, a grinding step of grinding the dried material, a classification step of adjusting the particle size of the ground material within an appropriate particle size range, a surface-crosslinking step of mixing a surface-crosslinking agent into the classified dried particles and heating the mixture, a sizing step of adjusting the particle sizes of the surface-crosslinked dried particles, and a fine powder collection step. In addition, in the reverse phase suspension polymerization method, a polymerization reaction is carried out in a state where a water-soluble ethylenically unsaturated monomer aqueous solution is dispersed as suspended particles in a hydrophobic organic solvent. Thus, a gel-crushing step during or after polymerization is generally unnecessary, but the subsequent production process includes steps that are substantially the same steps as in aqueous solution polymerization.

The amount of fine powder generated in a conventional production process reaches about 10% by mass to several tens of percentages by mass (for example, 20 to 30% by mass) of the total quantity of production. For example, in the production process illustrated in FIG. 7, fine powder is also generated due to process damage in steps such as the surface-crosslinking step and the sizing step after the drying step and a transport step, in addition to the polymerization step and the grinding step. In particular, when fine powder is generated due to process damage in the surface-crosslinking step or a step subsequent thereto, destruction of the surface crosslinked structure also occurs, so that the physical properties of the water-absorbent resin may also be decreased.

Generated fine powder is removed in the classification step or the sizing step. Since disposal of the removed fine powder is disadvantageous in cost, the fine powder is recycled to a step before the classification step, particularly, in a step before the drying step, and further in the polymerization step, the gel-crushing step, and the drying step. However, the fine powder is likely to aggregate, and thus it is difficult to handle the fine powder. In addition, by adding a fine powder recycling step, the production process (facility) for a water-absorbent resin is further complicated or increased in size. Moreover, the load on the polymerization step or the drying step in which the fine powder is recycled is increased, and thus an increase in amount of the fine powder collected may be accompanied with a decrease in productivity or a decrease in performance of the obtained water-absorbent resin.

A method (Patent Literature 1) using a stirring drying device provided with stirring plates including scooping blades or provided with crushing means between stirring plates, in order to inhibit generation of coarse particles in a surface-crosslinking step and reduce the amount of fine powder generated by crushing coarse particles in a subsequent sizing step, and a method (Patent Literature 2) using a stirring device having a specific structure in order to shorten the treatment time in a surface-crosslinking step and inhibit generation of fine powder due to mechanical damage from stirring plates, have been proposed. In addition, a method of heating water-absorbent polymer particles using a fluidized bed drying machine has been proposed (Patent Literature 3).

CITATION LIST

Patent Literature

Patent Literature 1: JP2004-352941
Patent Literature 2: JP2008-38128
Patent Literature 3: JP Patent No. 5918864

SUMMARY OF THE INVENTION

Problems to be Solved by the Invention

In recent years, in the case of industrially producing a water-absorbent resin, from the viewpoint of production efficiency and cost reduction, stable production of a water-absorbent resin having target physical properties is essential in the production process including steps from a polymerization step to a fine powder collection step. In the case where the stirring drying device described in Patent Literature 1 or 2 is used in a surface-crosslinking step, mechanical damage from the stirring plates is still unavoidable, and it is difficult to reduce the amount of fine powder generated to the required amount. In particular, it has been found that, when the production is scaled up, the retention time of water-absorbent resin particles within the device becomes longer, so that mechanical damage to the water-absorbent resin particles increases and the amount of fine powder generated increases. In particular, it has been found that, during production of a water-absorbent resin in the form of granulated or foamed particles which is a product having a high water absorption speed, the process damage increases and the amount of fine powder generated further increases. Furthermore, it has been found that, with the stirring drying device of Patent Literature 1 or 2, it takes time to discharge the water-absorbent resin particles remaining in the device at the end of operation, and thus problems such as a decrease in physical properties and increase of colored foreign matter due to excessive heating arise in addition to mechanical damage. Moreover, it has been found that, in the case where the fluidized bed described in Patent Literature 3 is used in the surface-crosslinking step, there is a problem that stirring is not sufficient and coarse particles are generated, so that the load in a sizing step increases. In particular, it has been found that, when the production is scaled up, due to insufficient stirring and heating, the retention time of water-absorbent resin particles becomes longer, the retention time distribution becomes wider, and problems such as a decrease in physical properties and increase of colored foreign matter arise.

Therefore, an object of the present invention is to provide an industrial production method for water-absorbent resin particles in which the amount of fine powder generated in a production procedure is small, a decrease in physical properties due to fine powder is inhibited, and the amount of colored foreign matter generated is small. Another object of the present invention is to provide a heating device and a surface-crosslinking method used in a surface-crosslinking step.

Solution to the Problems

As a result of thorough research, the present inventors have found that, by heating a mixture of a surface-crosslinking agent and a particulate dried polymer having a predetermined moisture content using a heating device having a specific structure, mechanical and thermal damage to water-absorbent resin particles is reduced, and the amount of fine powder generated and the amount of colored foreign matter are reduced, whereby the present inventors have completed the present invention. Furthermore, the present inventors have found that the advantageous effects of the present invention become more significant in scaled-up production of water-absorbent resin particles.

Specifically, the present invention is directed to a method for producing water-absorbent resin particles, the method including: a surface-crosslinking step of heating a mixture of a surface-crosslinking agent and a particulate dried polymer obtained with an acid group-containing unsaturated monomer as a main component and having a moisture content of not greater than 15% by mass, wherein a heating device including a rotary container and a plurality of heating tubes that are located within the rotary container, extend in an axial direction of the rotary container, and rotate together with the rotary container, is used in the surface-crosslinking step.

The present invention is also directed to a heating device for heating a mixture of a surface-crosslinking agent and a particulate dried polymer obtained with an acid group-containing unsaturated monomer as a main component and having a moisture content of not greater than 15% by mass, the heating device including: a rotary container; a plurality of heating tubes that are located within the rotary container, extend in an axial direction of the rotary container, and rotate together with the rotary container; and a means for introducing and discharging a gas into and from the rotary container.

The present invention is further directed to a surface-crosslinking method for heating a mixture of a surface-crosslinking agent and a particulate dried polymer obtained with an acid group-containing unsaturated monomer as a main component and having a moisture content of not greater than 15% by mass, using the above-described heating device, the surface-crosslinking method including causing a temperature of an inner surface of the rotary container to be not lower than 100° C.

Advantageous Effects of the Invention

With the production method according to the present invention, by using the heating device having a specific structure in the surface-crosslinking step, particularly, in a heating step of heating the mixture of the particulate dried polymer and the surface-crosslinking agent, mechanical damage to the water-absorbent resin particles is reduced, and generation of fine powder is inhibited. In addition, the load in a sizing step is low, and a decrease in physical properties due to destruction of surface-crosslink is inhibited. Furthermore, with the production method, also at the time of scaled-up production, the retention time of the water-absorbent resin particles within the heating device does not become excessively long, and thus the amount of fine powder generated is reduced. Moreover, with the heating device having the specific structure, the time for discharging the water-absorbent resin particles after the end of operation is appropriate, and thus generation of colored foreign matter due to excessive heating is inhibited, so that the production efficiency improves.

DESCRIPTION OF EMBODIMENTS

Figure 1:
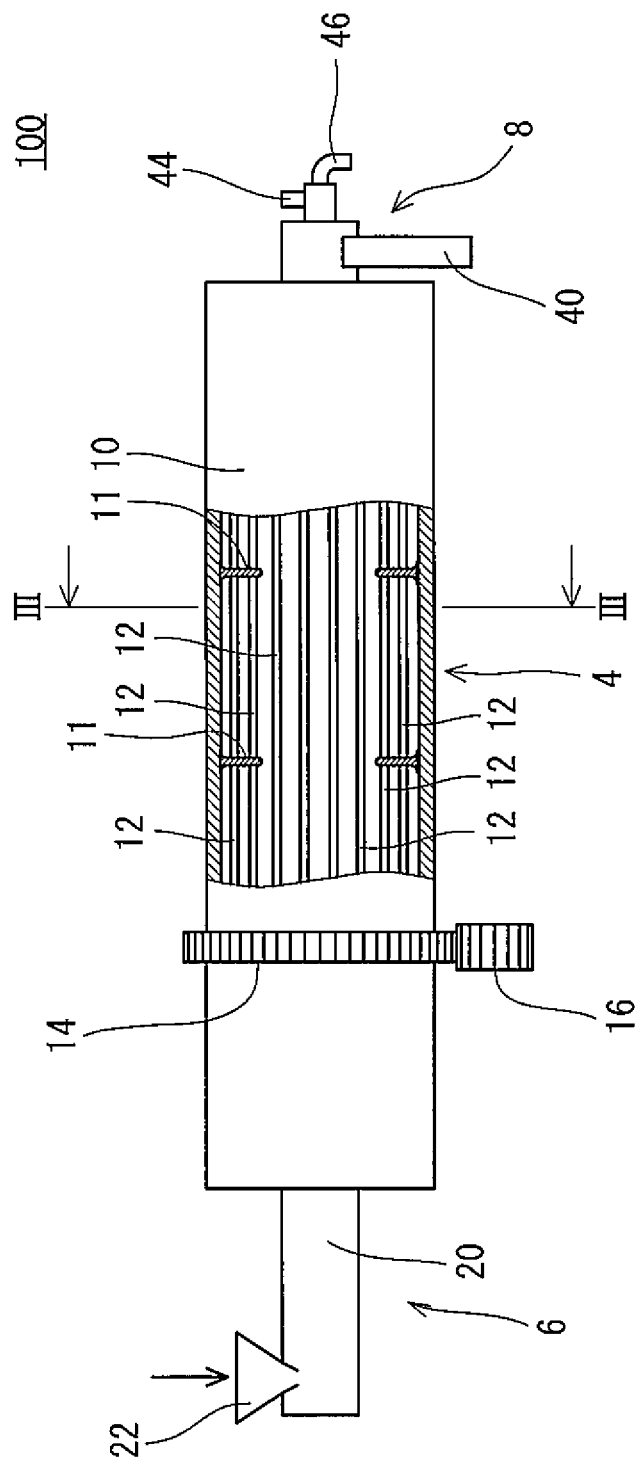
FIG. 1 is a partially cutaway side view showing an example of a heating device (rotary heating device with heating tubes) used in the production method according to the present invention.

The following will describe in detail the present invention. However, the scope of the present invention is not limited to the following description, and the present invention may be carried out by making modifications as appropriate without impairing the gist of the present invention, in addition to the following examples. Moreover, the present invention is not limited to the following embodiments, and various modifications may be made within the scope indicated by the claims. Another embodiment achieved by combining, as appropriate, each technical means disclosed in a plurality of embodiments is also included within the technical scope of the present invention.

[1] Definition of Terms

[1-1] "Water-Absorbent Resin"

The term "water-absorbent resin" in the present invention refers to a water-swellable and water-insoluble polymer gelling agent that satisfies the following physical properties. That is, "water-absorbent resin" refers to a polymer gelling agent whose CRC (centrifuge retention capacity) defined by ERT441.2-02 as water swellability is not less than 5 g/g and whose Ext (water-soluble content) defined by ERT470.2-02 as water insolubility is not greater than 50% by mass.

The water-absorbent resin can be designed as appropriate in accordance with the application and/or purpose thereof, and is not particularly limited but is preferably a hydrophilic crosslinked polymer obtained by crosslinking and polymerizing an unsaturated monomer including a carboxyl group. In addition, the water-absorbent resin is not limited to a resin entirely composed of a crosslinked polymer, and may be a composition containing an additive and the like as long as each of the above physical properties (CRC, Ext) satisfies the above numerical range.

In the present invention, in the case of being referred to as a "water-absorbent resin", the term "water-absorbent resin" may be a water-absorbent resin that is surface-crosslinked (also referred to post-crosslinked, secondarily crosslinked), or may be a water-absorbent resin that is not surface-crosslinked. In the present invention, in particular, in the case of being referred to as "water-absorbent resin particles" or a "water-absorbing agent", the term "water-absorbent resin particles" or "water-absorbing agent" means a water-absorbent resin that has undergone predetermined surface-crosslinking treatment and/or a water-absorbent resin that has undergone predetermined surface treatment and whose particle size has been adjusted.

[1-2] "Poly(Meth)Acrylic Acid (Salt)"

The term "poly(meth)acrylic acid (salt)" in the present invention refers to a poly(meth)acrylic acid and/or a salt thereof, and means a crosslinked polymer that contains a repeating unit of (meth)acrylic acid and/or a salt thereof (hereinafter, also referred to as a "(meth)acrylic acid (salt)") as a main component and that contains a graft component as an optional component.

The term "main component" means that the used amount (contained amount) of the (meth)acrylic acid (salt) with respect to the entire monomer (all monomers excluding a crosslinking agent) to be used in polymerization is preferably 50% by mole to 100% by mole, more preferably 70% by mole to 100% by mole, further preferably 90% by mole to 100% by mole, and particularly preferably substantially 100% by mole.

The term "poly(meth)acrylic acid (salt)" may be non-neutralized, but is preferably a partially neutralized or completely neutralized poly(meth)acrylic acid salt, more preferably a monovalent salt, further preferably an alkali metal salt or ammonium salt, particularly preferably alkali metal salt, and more particularly preferably a sodium salt.

[1-3] Definition of Evaluation Methods

The term "EDANA" is an abbreviation for the European Disposables and Nonwovens Association. The term "ERT" is an abbreviation for EDANA Recommended Test Methods and is a European standard that defines evaluation methods for water-absorbent resin. In the present invention, unless otherwise specified, regarding measuring methods that are described in the ERT original text (revised in 2002), measurement is performed according to the ERT original text. Regarding evaluation methods that are not described in the ERT original text (revised in 2002), measurement is performed by methods and conditions described in Examples.

[1-3-1] "CRC" (ERT441.2-02)

The term "CRC" is an abbreviation for Centrifuge Retention Capacity, and means the water absorption capacity under no load (sometimes also referred to as "water absorption capacity") of the water-absorbent resin. Specifically, CRC refers to a water absorption capacity (unit: g/g) measured after 0.2 g of the water-absorbent resin put in a bag made of a nonwoven fabric is immersed in a large excess of a 0.9% by mass sodium chloride aqueous solution for 30 minutes to be freely swollen and then drained in a centrifuge (250 G) for 3 minutes. For a hydrous gel after polymerization and/or after gel-crushing, CRC is obtained by using 0.4 g of the hydrous gel, changing the measuring time to 24 hours, and performing correction in terms of solid content.

[1-3-2] "Ext" (ERT470.2-02)

The term "Ext" is an abbreviation for Extractables, and means the water-soluble content (water-soluble polymer amount in water-absorbent resin) of the water-absorbent resin. Specifically, Ext refers to the amount (unit: % by mass) of substances dissolved in 200 ml of a 0.9% by mass sodium chloride aqueous solution after 1.0 g of the water-absorbent resin is added to the aqueous solution and the aqueous solution is stirred at 500 rpm for 16 hours. For measuring the water-soluble content, pH titration is used.

For a hydrous gel after polymerization and/or after gel-crushing, measurement is performed using 2.0 g of the hydrous gel, and Ext is calculated as a percentage by mass of water-soluble content per solid content.

[1-3-3] "Moisture Content" (ERT430.2-02)

The term "Moisture Content" means the moisture content, defined by a drying loss, of the water-absorbent resin. Specifically, the moisture content refers to a value (unit: % by mass) calculated from a drying loss when 4.0 g of the water-absorbent resin is dried at 105° C. for 3 hours. In the present invention, for a water-absorbent resin after drying, the moisture content is defined by a drying loss from 1.0 g of the water-absorbent resin at 180° C. for 3 hours, and for a hydrous gel before drying, the moisture content is defined by a drying loss from 2.0 g of the hydrous gel at 180° C. for 24 hours.

[1-3-4] "PSD" (ERT420.2-02)

The term "PSD" is an abbreviation for Particle Size Distribution, which means the particle size distribution of the water-absorbent resin measured by sieve classification. A mass-average particle diameter (D50) and the logarithmic standard deviation (σζ) of the particle size distribution are measured by the same method as described in U.S. Pat. No. 7,638,570. In the present invention, the particle size distribution (PSD) of a particulate hydrous gel is defined by sieve classification performed in a wet process by a method described later. Furthermore, the particle diameter (μm) of a particulate hydrous gel in terms of solid content is defined by a later-described calculation method from the particle diameter (μm) of the particulate hydrous gel and the solid content rate (% by mass) thereof.

[1-3-5] "AAP" (ERT442.2-02)

The term "AAP" is an abbreviation for Absorption Against Pressure, and means the water absorption capacity under load of the water-absorbent resin. Specifically, AAP refers to a water absorption capacity (unit: g/g) measured after 0.9 g of the water-absorbent resin is swollen in a large excess of a 0.9% by mass sodium chloride aqueous solution for 1 hour under a load of 2.06 kPa (21 $g/cm^2$, 0.3 psi). In the specification of the present application, AAP is defined as a value measured by changing the load condition to 4.83 kPa (equivalent to about 49 $g/cm^2$, or about 0.7 psi).

[1-3-6] "Residual Monomers" (ERT410.2-02)

The term "Residual Monomers" means the ratio (unit: ppm) of the mass of the monomer remaining in the water-absorbent resin (hereinafter, referred to as "residual monomer") to the mass of the water-absorbent resin. Specifically, 1.0 g of the water-absorbent resin is added to 200 ml of a 0.9% by mass sodium chloride aqueous solution, and the amount of the monomer eluted after stirring for 1 hour is measured using high performance liquid chromatography. The residual monomers of a hydrous gel are defined as the ratio (unit: % by mass) of a residual monomer mass obtained by performing measurement by a method described below to the mass of the resin solid content of the hydrous gel after performing a polymerization termination operation such as forced cooling or the like as necessary.

[1-4] Others

In the present specification, "X to Y" indicating a range means "not less than X and not greater than Y". Unless otherwise noted, the mass unit "t (ton)" refers to "metric ton", and "ppm" refers to "ppm by mass" or "ppm by weight". Furthermore, "mass" and "weight", "part(s) by mass" and "part(s) by weight", and "% by mass" and "% by weight" are synonymous with each other. Moreover, " . . . acid (salt)" means " . . . acid and/or a salt thereof", and "(meth)acrylic" means "acrylic and/or methacrylic".

[2] Method for Producing Water-Absorbent Resin Particles

The method for producing water-absorbent resin particles according to the present invention includes a surface-crosslinking step of heating a mixture of a surface-crosslinking agent and a particulate dried polymer obtained with an acid group-containing unsaturated monomer as a main component. The surface-crosslinking step preferably includes a surface-crosslinking agent adding step and a heat treatment step. Preferably, this production method further includes a polymerization step, a gel-crushing step (performed simultaneously with or separately from polymerization), a drying step, a cooling step (performed after drying and/or after surface-crosslinking), and a sizing step (performed after drying and/or after surface-crosslinking). In addition, this production method may include a step of preparing a monomer aqueous solution, a step of adding various additives, a fine powder removing step, and a fine powder recycling step. Furthermore, this production method can include various publicly known steps according to the purpose. The surface-crosslinking step in the present invention means a step performed separately from a drying step after the drying step.

The following will describe each step in detail.

[2-1] Step of Preparing Monomer Aqueous Solution

This step is a step of preparing an aqueous solution that contains an acid group-containing unsaturated monomer as a main component (hereinafter, referred to as a "monomer aqueous solution"). A slurry liquid of the monomer can be also used as long as the fluid retention performance of the obtained water-absorbent resin is not decreased. In this section, for the sake of convenience, the monomer aqueous solution will be described.

The term "main component" means that the used amount (contained amount) of the acid group-containing unsaturated monomer with respect to the entire monomer (excluding an internal crosslinking agent) to be subjected to a polymerization reaction for a water-absorbent resin is normally not less than 50% by mole, preferably not less than 70% by mole, and more preferably not less than 90% by mole (the upper limit is 100% by mole).

(Acid Group-Containing Unsaturated Monomer)

The acid group defined in the present invention is not particularly limited, and examples thereof include a carboxyl group, a sulfone group, and a phosphoric acid group. Examples of the acid group-containing unsaturated monomer include (meth)acrylic acid, maleic acid (anhydride), itaconic acid, cinnamic acid, vinylsulfonic acid, allyltoluene sulfonic acid, vinyltoluene sulfonic acid, styrene sulfonic acid, 2-(meth)acrylamide-2-methylpropane sulfonic acid, 2-(meth)acryloylethane sulfonic acid, 2-(meth)acryloylpropane sulfonic acid, 2-hydroxyethyl(meth)acryloyl phosphate, and the like. From the viewpoint of fluid retention performance, (meth)acrylic acid, maleic acid (anhydride), itaconic acid, and cinnamic acid are preferable, and (meth)acrylic acid is more preferable.

(Monomer Other than Acid Group-Containing Unsaturated Monomer)

A monomer other than the acid group-containing unsaturated monomer may be any compound that can be polymerized into a water-absorbent resin. Examples of such a monomer include: amide group-containing unsaturated monomers such as (meth)acrylamide, N-ethyl(meth)acrylamide, and N,N-dimethyl(meth)acrylamide; amino group-containing unsaturated monomers such as N,N-dimethylaminoethyl(meth)acrylate, N,N-dimethylaminopropyl (meth)acrylate, and N,N-dimethylaminopropyl(meth)acrylamide; mercapto group-containing unsaturated monomers; phenolic hydroxyl group-containing unsaturated monomers; lactam group-containing unsaturated monomers such as N-vinylpyrrolidone; and the like.

(Polymerization Inhibitor)

The monomer to be used for polymerization preferably contains a small amount of a polymerization inhibitor from the viewpoint of stability of polymerization. A preferable polymerization inhibitor is p-methoxyphenol. The amount of the polymerization inhibitor contained in the monomer (particularly, acrylic acid and a salt thereof) is normally 1 ppm to 250 ppm, preferably 10 ppm to 160 ppm, and more preferably 20 ppm to 80 ppm.

(Neutralized Salt)

In the present invention, a neutralized salt obtained by neutralizing a part or the entirety of the acid group included in the acid group-containing unsaturated monomer can be used. In this case, a salt of the acid group-containing unsaturated monomer is preferably a salt with monovalent cations, more preferably at least one salt selected from an alkali metal salt, an ammonium salt, and an amine salt, further preferably an alkali metal salt, even further preferably at least one salt selected from a sodium salt, a lithium salt, and a potassium salt, and particularly preferably a sodium salt.

(Basic Substance)

A neutralizer to be used for neutralizing the above acid group-containing unsaturated monomer is not particularly limited, but an inorganic salt such as sodium hydroxide, potassium hydroxide, sodium carbonate, and ammonium carbonate, a basic substance such as an amine-based organic compound having an amino group or an imino group, or the like is selected as appropriate and used as the neutralizer. As the neutralizer, two or more basic substances may be used in combination. Unless otherwise specified, the monomer in the present invention is a concept including a neutralized salt thereof.

(Neutralization Ratio)

From the viewpoint of fluid retention performance, the number of moles of the neutralized salt with respect to the total number of moles of the acid group-containing unsaturated monomer and the neutralized salt thereof (hereinafter, referred to as "neutralization ratio") is preferably not less than 40% by mole, more preferably 40% by mole to 80% by mole, further preferably 45% by mole to 78% by mole, and particularly preferably 50% by mole to 75% by mole.

Examples of the method for adjusting the neutralization ratio include: a method in which the acid group-containing unsaturated monomer and the neutralized salt thereof are mixed with each other; a method in which a publicly known neutralizer is added to the acid group-containing unsaturated monomer; a method in which a partially neutralized salt of the acid group-containing unsaturated monomer that is adjusted in advance to a predetermined neutralization ratio (i.e., a mixture of the acid group-containing unsaturated monomer and the neutralized salt thereof) is used; and the like. In addition, these methods may be combined.

The adjustment of the neutralization ratio may be performed before initiation of a polymerization reaction of the acid group-containing unsaturated monomer, may be performed during a polymerization reaction of the acid group-containing unsaturated monomer, or may be performed on a crosslinked hydrogel polymer obtained after end of the polymerization reaction of the acid group-containing unsaturated monomer. In addition, the neutralization ratio may be adjusted at any one stage selected from among: before initiation of the polymerization reaction; during the polymerization reaction; and after end of the polymerization reaction, or the neutralization ratio may be adjusted at a plurality of stages among them. In application to absorbent articles such as disposable diapers and the like in which there is a possibility of direct contact with a human body, the neutralization ratio only needs to be adjusted preferably before initiation of the polymerization reaction and/or during the polymerization reaction, and more preferably before initiation of the polymerization reaction.

(Internal Crosslinking Agent)

In the method for producing the water-absorbent resin particles, an internal crosslinking agent is preferably used. By the internal crosslinking agent, the fluid retention performance of the obtained water-absorbent resin, the gel strength thereof at the time of water absorption, and the like are adjusted.

The internal crosslinking agent only needs to have two or more unsaturated bonds or reactive functional groups in total within one molecule thereof. Examples of an internal crosslinking agent having a plurality of polymerizable unsaturated groups (that are polymerizable with the monomer) within the molecule thereof include N,N-methylene bis (meth)acrylamide, (poly)ethylene glycol di(meth)acrylate, (poly) propylene glycol di(meth)acrylate, trimethylol propane tri(meth)acrylate, glycerin (meth)acrylate, glycerin acrylate methacrylate, ethylene oxide-modified trimethylol propane tri(meth)acrylate, pentaerythritol hexa(meth)acrylate, triallyl cyanurate, triallyl isocyanurate, triallyl phosphate, and the like. Examples of an internal crosslinking agent having a plurality of reactive functional groups (that can react with a functional group (for example, a carboxy group) of the monomer) within the molecule thereof include triallylamine, polyallyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, and the like (here, a cyclic carbonate such as ethylene carbonate and the like is a crosslinking agent that reacts with a carboxyl group, thereby further generating a functional group OH). Examples of an internal crosslinking agent having a polymerizable unsaturated group and a reactive functional group within the molecule thereof include glycidyl (meth)acrylate and the like. Two or more of them may be used in combination.

Among these internal crosslinking agents, from the viewpoint of the advantageous effects of the present invention, a compound having a plurality of polymerizable unsaturated groups within the molecule thereof is preferable, a compound having a (poly)alkylene structural unit within the molecule thereof is more preferable, a compound having a polyethylene glycol structural unit is further preferable, and an acrylate compound having a polyethylene glycol structural unit is particularly preferable. A hydrous gel obtained by using these internal crosslinking agents has low water absorption capacity at the initial stage of drying, and has low adhesiveness. In the case of performing stirring drying on the hydrous gel having low adhesiveness, fusion or aggregation during drying can be reduced, and thus such drying is preferable. Furthermore, with the hydrous gel obtained by using these internal crosslinking agents, an effect that the water absorption capacity is easily improved is exhibited by drying.

The used amount of the internal crosslinking agent is set as appropriate in accordance with the types of the monomer and the internal crosslinking agent and the like. From the viewpoint of the gel strength of the obtained water-absorbent resin, the used amount of the internal crosslinking agent with respect to the monomer is preferably not less than 0.001% by mole, more preferably not less than 0.005% by mole, and further preferably not less than 0.01% by mole. In addition, from the viewpoint of improvement of the fluid retention performance of the water-absorbent resin, the used amount of the internal crosslinking agent is preferably not greater than 5% by mole and more preferably not greater than 2% by mole. In a polymerization condition in which a self-crosslinking reaction of the monomer is effective, the internal crosslinking agent may not be used.

(Other Substances)

In the production method according to the present invention, substances (hereinafter, referred to as "other substances") whose examples will be described below can be also added to the monomer aqueous solution as long as the objects of the present invention are achieved.

Specific examples of the other substances include: chain transfer agents such as thiols, thiolic acids, secondary alcohols, amines, and hypophosphites; foaming agents such as carbonates, bicarbonates, azo compounds, and bubbles; chelating agents such as ethylene diamine tetra(methylene phosphinic acid) and metal salts thereof, ethylenediamine tetraacetic acid and metal salts thereof, and diethylenetriamine pentaacetic acid and metal salts thereof; hydrophilic polymers such as polyacrylic acid (salt) and crosslinked products thereof (for example, water-absorbent resin fine powder to be recycled), starch, cellulose, starch-cellulose derivatives, and polyvinyl alcohol; and the like. The other substances may be used solely, or two or more of the other substances may be used in combination.

The used amount of the other substances is not particularly limited, but the amount of fine powder to be recycled with respect to the monomer is not greater than 30% by mass, and the total concentration of the other substances other than the fine powder with respect to the monomer is preferably not greater than 10% by mass, more preferably 0.001% by mass to 5% by mass, and particularly preferably 0.01% by mass to 1% by mass.

(Monomer Concentration in Monomer Aqueous Solution)

In this step, from the viewpoint of the physical properties and the productivity of the water-absorbent resin, the monomer concentration in the monomer aqueous solution (=total monomer amount/(total monomer amount+total polymerization solvent amount (normally, water))) is preferably 10% by mass to 90% by mass, more preferably 20% by mass to 80% by mass, further preferably 30% by mass to 70% by mass, and particularly preferably 40% by mass to 60% by mass. Hereinafter, this monomer concentration is sometimes referred to merely as "monomer concentration".

(Polymerization Initiator)

The polymerization initiator to be used in the present invention is selected as appropriate in accordance with the type of polymerization or the like, and thus is not particularly limited, but examples of the polymerization initiator include pyrolytic polymerization initiators, photolytic polymerization initiators, or a combination thereof; or redox polymerization initiators in which these polymerization initiators and the reducing agents that promote decomposition of these polymerization initiators are used in combination.

Specifically, one of the polymerization initiators described in U.S. Pat. No. 7,265,190, or two or more thereof are used. From the viewpoint of the handleability of the polymerization initiator and the physical properties of the water-absorbent resin, a peroxide or an azo compound is preferably used, a peroxide is more preferably used, and a persulfate is further preferably used.

The used amount of the polymerization initiator with respect to the monomer is preferably 0.001% by mole to 1% by mole and more preferably 0.001% by mole to 0.5% by mole. In addition, in the case of carrying out redox polymerization as necessary, the used amount of the reducing agent used in combination with an oxidizing agent, with respect to the monomer, is preferably 0.0001% by mole to 0.02% by mole.

(Dissolved Oxygen Amount)

Oxygen dissolved in the monomer aqueous solution before polymerization is also preferably reduced by temperature increase or substitution with an inert gas. For example, the dissolved oxygen is reduced to preferably 5 ppm or less, more preferably 3 ppm or less, and particularly preferably 1 ppm or less.

Bubbles (particularly, the above inert gas, etc.) can be dispersed in the monomer aqueous solution. In this case, foaming polymerization occurs in the polymerization reaction.

[2-2] Polymerization Step

This step is a step of polymerizing the monomer aqueous solution to obtain a crosslinked hydrogel polymer (in the specification of the present application, sometimes referred to as a "hydrous gel").

In addition to the method of carrying out a polymerization reaction by adding the polymerization initiator, there is a method of applying active energy rays such as radiation, electron rays, ultraviolet rays, and the like. Moreover, after the polymerization initiator is added, application of active energy rays may be used in combination.

(Type of Polymerization)

The type of polymerization is not particularly limited. From the viewpoint of fluid retention performance, ease of polymerization control, and the like, examples of the type of polymerization are preferably droplet polymerization in vapor phase, aqueous solution polymerization, and reverse phase suspension polymerization (droplet polymerization in the hydrophobic organic solvent is also included in examples of reverse phase suspension polymerization), more preferably aqueous solution polymerization and reverse phase suspension polymerization, and further preferably aqueous solution polymerization. Among them, continuous aqueous solution polymerization is particularly preferable, and examples thereof include continuous belt polymerization and continuous kneader polymerization. By adopting continuous aqueous solution polymerization, the production efficiency of the water-absorbent resin is improved.

Examples of preferable types of the above continuous aqueous solution polymerization include "high-temperature-initiation polymerization" and "high-concentration polymerization". The term "high-temperature-initiation polymerization" refers to a type of polymerization in which polymerization is initiated when the temperature of the monomer aqueous solution is preferably not lower than 30° C., more preferably not lower than 35° C., further preferably not lower than 40° C., and particularly preferably not lower than 50° C. (the upper limit is the boiling point of the monomer aqueous solution). The term "high-concentration polymerization" refers to a type of polymerization in which polymerization is carried out when the monomer concentration is preferably not less than 30% by mass, more preferably not less than 35% by mass, further preferably not less than 40% by mass, and particularly preferably not less than 45% by mass (the upper limit is the saturation concentration). These types of polymerization can be used in combination.

In droplet polymerization in vapor phase, polymerization can be carried out in the air atmosphere. However, from the viewpoint of the color tone of the obtained water-absorbent resin, polymerization can be preferably carried out in an inert gas atmosphere such as nitrogen, argon, and the like. In this case, for example, the concentration of oxygen in vapor phase is preferably controlled to be not greater than 1% by volume.

(Polymerization Ratio of Hydrous Gel)

The polymerization ratio of the crosslinked hydrogel polymer obtained in the polymerization step is preferably not less than 90% by mass, more preferably not less than 95% by mass, further preferably not less than 98% by mass, and particularly preferably not less than 99% by mass, from the viewpoint of inhibition of aggregation during drying of the particulate crosslinked hydrogel polymer obtained in the next gel-crushing step or a reduction in the residual monomer in the obtained water-absorbent resin. After the polymerization step, when a hydrous gel having a low polymerization ratio is crushed and a drying step is carried out in a state where a large amount of unreacted monomer is included, a polymerization reaction proceeds during drying, and gel particles having a large particle diameter are regenerated from gel particles having a small particle diameter, so that problems such as a decrease in the water absorption speed of the obtained water-absorbent resin, an increase in the particle diameter of the dried material, and the like arise.

(Physical Properties of Hydrous Gel)

The CRC (centrifuge retention capacity) of the crosslinked hydrogel polymer obtained in the polymerization step, in terms of solid content, is preferably 5 g/g to 80 g/g, more preferably 10 g/g to 50 g/g, further preferably 15 g/g to 45 g/g, and particularly preferably 20 g/g to 40 g/g. In addition, the water-soluble content of the crosslinked hydrogel polymer obtained in the polymerization step is preferably 1% by mass to 20% by mass, more preferably 2% by mass to 15% by mass, and further preferably 3% by mass to 10% by mass. When the CRC and/or the water-soluble content exceeds the above range, the crushed hydrous gel particles exhibit adhesiveness, and the fluidity of the particulate hydrous gel decreases.

[2-3] Gel-Crushing Step

This step is a step of grinding and finely granulating the crosslinked hydrogel polymer obtained in the polymerization step, simultaneously with and/or after polymerization, and is a step of grinding the crosslinked hydrogel polymer by a screw extruder such as a kneader, a meat chopper, and the like, or a device such as a cutter mill and the like, to obtain a particulate crosslinked hydrogel polymer (hereinafter, referred to as a "particulate hydrous gel"). The particle diameter of the particulate hydrous gel is adjusted to be within a later-described preferable range such that water-absorbent resin particles having a target shape and performance are obtained in high yield. This step may be carried out twice or more in order to obtain a particulate hydrous gel having a predetermined particle diameter. In addition, as in reverse phase suspension polymerization or vapor-phase polymerization, this step does not have to be carried out when a particulate hydrous gel having a target particle size is obtained in the polymerization step.

After the polymerization step and before the gel-crushing step, a shredding step of cutting or roughly crushing the crosslinked hydrogel polymer into a size that allows the crosslinked hydrogel polymer to be put into a gel-crushing device, may be carried out. In particular, when the polymerization step is belt polymerization and a sheet-shaped or block-shaped hydrous gel is obtained, the shredding step is preferably carried out. The means for cutting or roughly crushing the hydrous gel in the shredding step is not particularly limited, and a roller cutter, a guillotine cutter, a shredder cutter, and the like are used. The size to be shredded is not particularly limited as long as the size is within a range where the hydrous gel can be put into a later-described gel-crushing device, but the maximum diameter of the hydrous gel after shredding is preferably 1 mm to 3 m, more preferably 5 mm to 2.5 m, and particularly preferably 1 cm to 2 m. When the objects of the present invention are achieved, the shredding step does not have to be carried out.

(Gel-Crushing Device)

In the production method of the present invention, the type of the gel-crushing device is not particularly limited as long as a particulate hydrous gel having a predetermined particle size can be obtained without impairing the fluid retention performance. Examples thereof include a gel-crushing machine equipped with a plurality of rotary stirring blades such as a batch type or continuous type double-arm kneader and the like, a single-screw extruder, a twin-screw extruder, a meat chopper, and the like.

(Solid Content Rate of Hydrous Gel)

The solid content rate (hereinafter, gel solid content rate) of the hydrous gel to be subjected to the gel-crushing step is preferably not less than 25% by mass. From the viewpoint of inhibition of aggregation of hydrous gel particles after gel-crushing, the energy required for crushing, drying efficiency, and absorption performance, the gel solid content rate is more preferably 25% by mass to 75% by mass, further preferably 30% by mass to 70% by mass, even further preferably 35% by mass to 65% by mass, and particularly preferably 40% by mass to 60% by mass.

(Gel Fluidizer)

In the production method according to the present invention, before the gel-crushing step and/or during the gel-crushing step, a gel fluidizer may be added. Accordingly, the particulate hydrous gel containing the gel fluidizer is obtained. By adding the gel fluidizer, an effect that adhesion or bonding between hydrous gel particles is inhibited in a later-described drying step and the water absorption speed of the obtained water-absorbent resin is improved, is exhibited. In addition, an effect that the load in a later-described grinding step after drying is reduced and the amount of fine powder generated is reduced, is also exhibited. Furthermore, in the case of performing stirring drying in the drying step, the particle diameter of the obtained particulate dried polymer is closer to a product particle diameter, and thus the above effects become significant. From the viewpoint that each particle of the obtained particulate hydrous gel uniformly contains the gel fluidizer, the gel fluidizer is preferably added during the gel-crushing step. Even in the case where the gel-crushing step is not required, for example, in the case of performing reverse phase suspension polymerization in the polymerization step, the gel fluidizer is preferably added to the particulate hydrous gel at least before the drying step.

The addition amount of the gel fluidizer is set as appropriate in accordance with the moisture content of the hydrous gel or the particulate hydrous gel, or the type of the gel fluidizer. The addition amount with respect to the solid content of the hydrous gel is preferably 0.001% by mass to 0.5% by mass, more preferably 0.01% by mass to 0.3% by mass, and further preferably 0.02% by mass to 0.2% by mass.

Examples of the gel fluidizer include anionic, cationic, nonionic, and amphoteric surfactants, anionic, cationic, nonionic, and amphoteric low-molecular-weight or high-molecular-weight surfactants, polymer lubricants, and the like.

(Surfactant)

Specific examples of surfactants used as the gel fluidizer include (1) nonionic surfactants such as sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkylallylformaldehyde-condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphates of polyoxyethylene alkyl ethers, phosphates of polyoxyethylene alkyl aryl ethers, and the like, (2) amphoteric surfactants including: alkyl dimethylamino acetic acid betaines such as caprylic dimethylamino acetic acid betaine, lauryl dimethylamino acetic acid betaine, myristyl dimethylamino acetic acid betaine, stearyl dimethylamino acetic acid betaine, and the like; alkylamide propyl betaines such as lauric acid amide propyl betaine, coconut oil fatty acid amide propyl betaine, palm kernel oil fatty acid amide propyl betaine, and the like; alkyl hydroxy sulfobetaines such as lauryl hydroxy sulfobetaine and the like; alkyl carboxymethyl hydroxyethyl imidazolinium betaines such as 2-alkyl-N-carboxymethyl-N-hydroxyethyl imidazolinium betaine and the like; and the like, (3) anionic surfactants including alkyl amino monoalkali metal diacetates such as lauryl amino monosodium diacetate, lauryl amino potassium diacetate, myristyl amino sodium diacetate, and the like, and (4) cationic surfactants such as long-chain alkyl dimethylaminoethyl quaternary salts and the like. Two or more of these surfactants may be used in combination.

(Polymer Lubricant)

In the production method according to the present invention, a polymer lubricant whose examples will be described below can be added to the monomer aqueous solution or hydrous gel as long as the objects of the present invention are achieved.

Specific examples of the polymer lubricant include maleic anhydride-modified polyethylene, maleic anhydride-modified polypropylene, maleic anhydride-modified ethylene-propylene copolymer, maleic anhydride-modified ethylene-propylene-diene terpolymer (EPDM), maleic anhydride-modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylic acid copolymer, ethyl cellulose, ethyl hydroxyethyl cellulose, polyalkylene oxides such as polyethylene glycol, and the like. The molecular weights (weight-average molecular weights) of these polymer lubricants are each selected as appropriate from the range of preferably 200 to 2 million and more preferably 400 to one million. Two or more of these polymer lubricants may be used in combination.

As the gel fluidizer, these polymer lubricants and the above surfactants may be used in combination. In the case where a surfactant and a polymer lubricant are used in combination, the total addition amount thereof is set as appropriate in accordance with the type of polymerization, the composition of the monomer aqueous solution, and the moisture content of the hydrous gel. The total addition amount is set as a concentration with respect to the monomer component in the case where the surfactant and the polymer lubricant are added to the monomer aqueous solution, is set as a concentration with respect to the solid content rate of the hydrous gel in the case where the surfactant and the polymer lubricant are added to the hydrous gel, and is set as the sum of the above in the case where the surfactant and the polymer lubricant are added to both.

The total addition amount of the surfactant and the polymer lubricant is preferably not greater than 1.0% by mass and more preferably not greater than 0.5% by mass, and is preferably not less than 0.05% by mass and particularly preferably not less than 0.1% by mass.

(Surface Tension)

The type and the addition amount of the gel fluidizer are adjusted as appropriate in consideration of the fluidity of the particulate hydrous gel in the gel-crushing step and the drying step, and the like. The type and the amount of the gel fluidizer with which the surface tension of a water-absorbent resin that is a final product is not excessively decreased, are preferable in view of the amount of return from the obtained water-absorbent resin in an absorbent article (diaper) during actual use, and the like. For example, the type and the amount of the gel fluidizer are selected such that the surface tension of the water-absorbent resin (the surface tension of a dispersion liquid of the water-absorbent resin in a physiological saline solution) is preferably not less than 55 mN/m, more preferably not less than 60 mN/m, and further preferably not less than 65 mN/m. The surface tension is measured by the method described in WO2015/129917.

(Polymerization Ratio of Particulate Hydrous Gel)

In the production method according to the present invention, it is also possible to cause the polymerization reaction to proceed to adjust the polymerization ratio, while crushing the hydrous gel in the gel-crushing step. The degree of progress of the polymerization reaction is adjusted as appropriate on the basis of heating and retention time in the gel-crushing device, the amount of the polymerization initiator remaining in the hydrous gel after polymerization, the post-addition amount of an optional polymerization initiator, and the like. The polymerization ratio of the particulate hydrous gel obtained after gel-crushing, in terms of solid content, is preferably not less than 90% by mass, more preferably not less than 95% by mass, further preferably 98 to 99.99% by mass, and ideally 100%. In the particulate hydrous gel having a polymerization ratio within the above range, aggregation and adhesion during drying are avoided. The adjustment of the polymerization ratio of the particulate hydrous gel is particularly effective in the case of stirring drying. Similar to the polymerization ratio of the hydrous gel before gel-crushing, the polymerization ratio of the particulate hydrous gel is defined by a physical property measuring method described later.

(Moisture Content of Particulate Hydrous Gel)

The moisture content of the particulate hydrous gel (hereinafter, gel moisture content) is obtained by a measurement method described in Examples below. From the viewpoint of the fluidity of the particulate hydrous gel in the later-described drying step, the gel moisture content is preferably not less than 25% by mass, more preferably not less than 30% by mass, further preferably not less than 35% by mass, particularly preferably not less than 40% by mass, and extremely preferably not less than 43% by mass. Excessive high-concentration polymerization may decrease the physical properties of the water-absorbent resin. From the viewpoint of drying efficiency and absorption performance, the gel moisture content is preferably not greater than 75% by mass, more preferably not greater than 60% by mass, and particularly preferably not greater than 55% by mass.

(Particle Size of Particulate Hydrous Gel)

From the viewpoint of the water absorption speed and the particle diameter of the obtained water-absorbent resin and inhibition of generation of fine powder during crushing, a mass-average particle diameter d1 of the particulate cross-linked hydrogel polymer before drying, in terms of solid content, is preferably not greater than 3000 μm, more preferably not greater than 2000 μm, further preferably 50 μm to 1000 μm, and even further preferably 100 μm to 800 μm. The average particle diameter d1 of the particulate hydrous gel in terms of solid content is calculated from the mass-average particle diameter (D50) of the particulate hydrous gel by a method described in Examples below.

(Physical Properties of Particulate Hydrous Gel)

The CRC (centrifuge retention capacity) of the particulate hydrous gel before drying, in terms of solid content (defined by a measurement method described later), is preferably 5 g/g to 80 g/g, more preferably 10 g/g to 50 g/g, further preferably 15 g/g to 45 g/g, and particularly preferably 20 g/g to 40 g/g. The water-soluble content (Ext) of the particulate hydrous gel before drying, in terms of solid content (defined by a measurement method described later), is preferably 1% by mass to 15% by mass, more preferably 2% by mass to 10% by mass, and further preferably 3% by mass to 5% by mass.

[2-4] Drying Step

This step is a step of drying a particulate hydrous gel (preferably containing the gel fluidizer) to a desired moisture content to obtain a dried polymer, preferably a particulate dried polymer. The particulate hydrous gel to be subjected to this step is not limited to the particulate hydrous gel obtained through the gel-crushing step, and may be obtained, for example, by reverse phase suspension polymerization. In addition, the dried polymer obtained in this step may include granulated material (hereinafter, dried granulated particles) formed by a plurality of particles physically or chemically adhering to each other.

(Temperature of Particulate Hydrous Gel)

From the viewpoint of inhibition of aggregation of hydrous gel particles, a temperature T2 of the particulate hydrous gel to be subjected to the drying step is controlled to be preferably not lower than 50° C., more preferably not lower than 60° C., further preferably not lower than 70° C., particularly preferably not lower than 80° C., and most preferably not lower than 90° C. From the viewpoint of inhibition of coloring or performance decrease of the to-be-dried object, the temperature T2 is preferably not higher than 130° C., more preferably not higher than 110° C., and further preferably not higher than 105° C.

The drying method in the drying step of the present invention is not particularly limited, and ventilation drying, stirring drying, fluidized bed drying, and the like are used as appropriate. In addition, various drying methods such as heating drying, hot air drying, drying under reduced pressure, infrared drying, microwave drying, drum dryer drying, drying through azeotropic dehydration with a hydrophobic organic solvent, high humidity drying using high temperature steam, and the like can be adopted. From the viewpoint of drying efficiency, heating drying or hot air drying is preferable, and stirring-type heating drying, in which the to-be-dried object is dried while being moved, is more preferable.

(Drying Device)

The drying device used in the drying step is not particularly limited, and one or two or more of a heat transfer conduction type drying machine, a radiation heat transfer type drying machine, a hot air heat transfer type drying machine, a dielectric heating type drying machine, and the like are selected as appropriate. The drying device may be a batch type or a continuous type. In addition, the drying device may be a direct heating type or an indirect heating type. Examples thereof include heat transfer type drying machines such as through-flow band type, through-flow circuit type, through-flow vertical type, parallel flow band type, through-flow tunnel type, through-flow stirring type, through-flow rotation type, fluidized bed type, air flow type, and the like. In the case of a band type or the like in which drying is performed in a stationary state, large lump-shaped dried material is obtained, and thus a large amount of fine powder may be generated when the dried material is crushed to be processed into a particulate product. On the other hand, when a stirring drying machine including a flowing means for causing the to-be-dried object to flow in the drying machine (for example, a stirring blade provided in the drying machine or rotation of the drying machine itself) and one or more heating means is used, dried particles (hereinafter, sometimes referred to as particulate dried polymer) are obtained, and thus use of such a stirring drying machine is preferable, and a continuous stirring drying machine is more preferable. Preferable stirring drying methods are described in PCT/JP2017/041371 and PCT/JP2017/041372, and the description of such stirring drying can be used in the description of the present invention.

(Physical Properties of Dried Polymer)

The water-soluble content (Ext) of the dried polymer obtained in the drying step is preferably larger than the water-soluble content of the particulate hydrous gel before drying. The crosslinking density of the hydrous gel (particularly, the type and the amount of the internal crosslinking agent), the conditions for heating drying, etc., are adjusted such that the water-soluble content of the dried polymer obtained after drying, in terms of solid content, is increased by preferably +0.5% by mass or greater, more preferably +1 to 20% by mass, and further preferably +2 to 10% by mass.

By increasing the water-soluble content of the dried polymer from that of the particulate hydrous gel, the water absorption capacity (CRC) after drying is improved. And also, adhesion or aggregation during drying can be prevented, and thus such increasing is preferable. The water-soluble content of the obtained dried polymer is preferably not greater than 50% by mass, more preferably not greater than 25% by mass, further preferably not greater than 20% by mass, and particularly preferably not greater than 15% by mass.

[2-5] Grinding Step, Classification Step

This step is a step of grinding the dried polymer obtained in the drying step (grinding step) and adjusting the dried polymer to a particle size within a predetermined range (classification step) to obtain water-absorbent resin powder. Here, for the sake of convenience, the powdery water-absorbent resin before being surface-crosslinked is referred to as "water-absorbent resin powder".

Examples of the device used in the grinding step of the present invention include high-speed rotary grinders such as a roll mill, a hammer mill, a screw mill, a pin mill, and the like, a vibration mill, a knuckle type grinder, a cylindrical mixer, and the like. These devices may be used in combination as necessary.

The method for adjusting the particle size in the classification step of the present invention is not particularly limited, and examples thereof include sieve classification using a JIS standard sieve (JIS Z8801-1 (2002)), airflow classification, and the like. The adjustment of the particle size of the water-absorbent resin is not limited to the grinding step and the classification step, and can be carried out as appropriate in the polymerization step (particularly, reverse phase suspension polymerization or spray droplet polymerization) or in another step (for example, a granulation step, a fine powder collection step, or the like).

The weight-average particle diameter (D50) of the water-absorbent resin powder obtained in this step is preferably 200 to 600 μm, more preferably 200 to 500 μm, further preferably 250 to 500 μm, and particularly preferably 350 to 450 μm. The proportion of particles having a particle diameter of less than 150 μm is preferably not greater than 10% by mass, more preferably not greater than 5% by mass, and further preferably not greater than 1% by mass. The proportion of particles having a particle diameter of not less than 850 μm is preferably not greater than 5% by mass, more preferably not greater than 3% by mass, and further preferably not greater than 1% by mass. Each of the lower limits of the proportions of these particles is preferably lower and desirably 0% by mass, but may be about 0.1% by mass. Moreover, the logarithmic standard deviation ($\sigma\zeta$) of the particle size distribution is preferably 0.20 to 0.50, more preferably 0.25 to 0.40, and further preferably 0.27 to 0.35. These particle sizes are measured using standard sieves according to the methods described in U.S. Pat. No. 7,638,570 and EDANA ERT 420.2-02.

The above-described preferable particle size is applied not only to a water-absorbent resin (hereinafter, for the sake of convenience, sometimes referred to as "water-absorbent resin particles") after surface-crosslinking but also to a water-absorbent resin as a final product. Therefore, a surface-crosslinking step is preferably carried out such that the particle sizes of the water-absorbent resin particles are maintained within the above range, and the particle sizes of the water-absorbent resin particles are more preferably adjusted in a sizing step provided after the surface-crosslinking step.

[2-6] Surface-Crosslinking Step

In the production method according to the present invention, the surface-crosslinking step is a step performed separately from the above-described drying step, and includes a surface-crosslinking agent adding step of adding a surface-crosslinking agent that reacts with a functional group (particularly, a carboxyl group) of a water-absorbent resin, to the dried polymer, and a heat treatment step of heating the dried polymer containing the surface-crosslinking agent to cause a crosslinking reaction. This step is a step for providing a portion having a further high crosslinking density to a surface layer (a portion of several tens of micrometers from the surface of the water-absorbent resin powder) of the water-absorbent resin powder obtained through the above-described steps, and includes a surface-crosslinking agent adding step, a heat treatment step, and a cooling step which is optionally performed. In this surface-crosslinking step, a surface-crosslinked water-absorbent resin (water-absorbent resin particles) is obtained by a radical crosslinking reaction, a surface polymerization reaction, a crosslinking reaction with the surface-crosslinking agent, and the like on the surface of the water-absorbent resin powder.

[2-6-1] Surface-Crosslinking Agent Adding Step

This step is a step of adding the surface-crosslinking agent to the particulate dried polymer. The surface-crosslinking agent is added to the particulate dried polymer after drying or to the particulate dried polymer whose particle size is adjusted after drying.

(Moisture Content of Particulate Dried Polymer)

In the production method according to the present invention, the moisture content of the particulate dried polymer to be subjected to the surface-crosslinking agent adding step is not greater than 15% by mass. From the viewpoint of the fluid retention performance of the obtained water-absorbent resin particles, the moisture content of the particulate dried polymer is preferably not greater than 10% by mass, more preferably not greater than 7% by mass, and particularly preferably not greater than 5% by mass. From the viewpoint of prevention of excessive aggregation or adhesion, the moisture content preferably exceeds 1% by mass. The moisture content of the particulate dried polymer is obtained by a measurement method described in Examples below.

(Temperature of Particulate Dried Polymer)

The particulate dried polymer to be subjected to the surface-crosslinking agent adding step is preferably heated or thermally insulated. A temperature T3 of the particulate dried polymer is preferably 30 to 120° C., more preferably 35 to 80° C., and further preferably 40 to 70° C. If the temperature T3 of the particulate dried polymer to be subjected to this step is lower than 30° C., the surface-crosslinking treatment may become insufficient or non-uniform due to precipitation of the added surface-crosslinking agent, moisture absorption of the particulate dried polymer, or the like. In addition, if the temperature T3 exceeds 100° C., the surface-crosslinking agent may precipitate due to volatilization of water or a solvent in a surface-crosslinking agent solution.

Furthermore, a temperature T4 of a mixture of the particulate dried polymer and the surface-crosslinking agent obtained through this step is preferably 30 to 100° C., more preferably 30 to 90° C., and further preferably 30 to 80° C. When the temperature T4 is within the above range, the added surface-crosslinking agent effectively reacts in the later-described heat treatment step, and appropriate fluidity is maintained inside a heating device. Similar to the above-described temperature T2 of the particulate hydrous gel, the temperatures T3 and T4 are measured by a contact thermometer.

(Surface-Crosslinking Agent)

As the surface-crosslinking agent, a surface-crosslinking agent that can react with a plurality of functional groups of a water-absorbent resin (preferably, a plurality of carboxyl groups) is used, and a surface-crosslinking agent that can be covalently or ionically bound thereto and further can be covalently bound thereto is preferably used. Specific examples of the surface-crosslinking agent include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, and the like; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol polyglycidyl ether, glycidol, sorbitol polyglycidyl ether, pentaerythritol polyglycidyl ether, trimethylolpropane polyglycidyl ether, neopentyl glycol diglycidyl ether, 1,6-hexanediol diglycidyl ether, and the like; polyvalent amine compounds such as ethylene diamine, diethylene triamine, triethylene tetramine, tetraethylene pentamine, pentaethylene hexamine, polyethyleneimine, and the like, and inorganic salts or organic salts thereof; polyvalent isocyanate compounds such as 2,4-tolylene diisocyanate, hexamethylene diisocyanate, and the like; aziridine compounds such as polyaziridine and the like; polyvalent oxazoline compounds such as 1,2-ethylenebisoxazoline, bisoxazoline, polyoxazoline, and the like; carbonic acid derivatives such as urea, thiourea, guanidine, dicyandiamide, 2-oxazolidinone, and the like; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-dimethyl-1,3-dioxane-2-one, 1,3-dioxopan-2-one, and the like; haloepoxy compounds such as epichlorohydrin, epibromohydrin, α-methylepichlorohydrin, and the like, and polyvalent amine adducts thereof; oxetane compounds; silane coupling agents such as γ-glycidoxypropyltrimethoxysilane, γ-aminopropyltriethoxysilane, and the like; polyvalent metal compounds such as hydroxides, chlorides, sulfates, nitrates, carbonates, or the like of zinc, calcium, magnesium, aluminum, iron, zirconium, and the like; and the like. Two or more of them may be used in combination. Among the above surface-crosslinking agents, one or two or more surface-crosslinking agents selected from polyvalent metal ions, epoxy compounds, oxazoline compounds, and alkylene carbonate compounds are preferable.

(Surface-Crosslinking Agent Solution)

The addition amount of the surface-crosslinking agent with respect to the solid content of the particulate dried polymer is preferably not greater than 15% by mass, more preferably not greater than 10% by mass, and further preferably not greater than 2% by mass. The lower limit of the addition amount is preferably 0.001% by mass.

As the added form of the surface-crosslinking agent, the surface-crosslinking agent may be added as is. However, from the viewpoint of ease of addition, the surface-crosslinking agent is preferably dissolved in water or an organic solvent and added as a solution. The concentration of the surface-crosslinking agent solution is preferably 1 to 80% by mass, more preferably 5 to 60% by mass, further preferably 10 to 40% by mass, and particularly preferably 15 to 30% by mass.

The surface-crosslinking agent solution preferably contains water. The amount of the water with respect to the solid content of the particulate dried polymer is preferably 0.5 to 20% by mass and more preferably 0.5 to 10% by mass. In the case of adding the surface-crosslinking agent as an aqueous solution, the concentration of the aqueous solution can be adjusted in accordance with the moisture content of the particulate dried polymer at the time of contact with the surface-crosslinking agent, and thus addition of the surface-crosslinking agent as an aqueous solution is preferable.

In the case where a solution cannot be prepared since the solubility of the surface-crosslinking agent in water is low, a hydrophilic solvent such as alcohol or the like is preferably added as appropriate to obtain a homogeneous solution. In the case where the surface-crosslinking agent solution contains a hydrophilic organic solvent, the amount of the hydrophilic organic solvent with respect to the solid content of the particulate dried polymer is preferably 0 to 10% by mass and more preferably 0 to 5% by mass.

Examples of the hydrophilic organic solvent include primary alcohols having preferably 1 to 4 carbon atoms and more preferably 2 to 3 carbon atoms, lower ketones having 4 or less carbon atoms, and the like. Specific examples of the hydrophilic organic solvent include: lower alcohols such as methyl alcohol, ethyl alcohol, n-propyl alcohol, isopropyl alcohol, n-butyl alcohol, isobutyl alcohol, t-butyl alcohol, and the like; ketones such as acetone and the like; ethers such as dioxane, tetrahydrofuran, methoxy (poly)ethylene glycol, and the like; sulfoxides such as dimethyl sulfoxide and the like; and polyhydric alcohols such as polyoxypropylene, oxyethylene-oxypropylene block copolymers, and the like.

Unless the advantageous effects of the present invention are impaired, the surface-crosslinking agent solution may further contain water-insoluble fine particles, a surfactant, an organic acid or a salt thereof, an inorganic acid or a salt thereof, and an inorganic base.

The temperature of the surface-crosslinking agent solution to be added to the particulate dried polymer is determined as appropriate on the basis of the solubility or viscosity of the surface-crosslinking agent to be used. The temperature of the surface-crosslinking agent solution is preferably −10 to 100° C., more preferably 5 to 70° C., further preferably 10 to 65° C., and particularly preferably 25 to 50° C. If the temperature of the surface-crosslinking agent solution exceeds 100° C., the surface-crosslinking agent may be hydrolyzed before being mixed with the particulate dried polymer, or mixability with the particulate dried polymer may be decreased due to volatilization of water or an organic solvent. If the temperature of the surface-crosslinking agent solution is lower than −10° C., precipitation of the surface-crosslinking agent or solidification of the surface-crosslinking agent solution may occur.

(Method for Adding Surface-Crosslinking Agent)

The method for adding the surface-crosslinking agent to the particulate dried polymer is not particularly limited, and examples of the method include (1) a method of immersing the particulate dried polymer in a hydrophilic organic solvent and adsorbing the surface-crosslinking agent to the particulate dried polymer, (2) a method of directly spraying or dropping the surface-crosslinking agent solution onto the particulate dried polymer and mixing the particulate dried polymer and the surface-crosslinking agent solution, and the like. The method (2) is preferable from the viewpoint of uniformly adding a predetermined amount of the surface-crosslinking agent to the water-absorbent resin. From the same viewpoint, the particulate dried polymer is preferably stirred during addition of the surface-crosslinking agent solution, and the surface-crosslinking agent solution is more preferably added by spraying.

In the case of adding two or more types of surface-crosslinking agents or two or more types of surface-crosslinking agent solutions having different compositions in the surface-crosslinking agent adding step, for example, the surface-crosslinking agents or the surface-crosslinking agent solutions may be added simultaneously by using different spray nozzles. However, from the viewpoint of uniform addition, the different types of surface-crosslinking agents or surface-crosslinking agent solutions are preferably mixed in advance and added as a single surface-crosslinking agent or surface-crosslinking agent solution. In addition, in the case of adding a single surface-crosslinking agent or surface-crosslinking agent solution, a plurality of spray nozzles may be used in consideration of the size of an adding device, the addition amount, the spray angle of each spray nozzle, and the like.

Examples of the adding device (hereinafter, also referred to as mixing device) used in the surface-crosslinking agent adding step include a cylindrical mixer, a double walled conical mixer, a V-shaped mixer, a ribbon mixer, a screw mixer, a flow furnace rotary disk mixer, an airflow mixer, a double-arm kneader, an internal mixer, a pulverizing kneader, a rotary mixer, a screw extruder, a turbulizer, a proshare mixer, and the like. For large-scale production such as commercial production, devices capable of continuous mixing are preferable. In the surface-crosslinking agent adding step, the surface-crosslinking agent may be added in a later-described heating device.

(Number of Times of Addition of Surface-Crosslinking Agent)

The number of times of addition of the surface-crosslinking agent in the surface-crosslinking step performed separately after the drying step may be one or a plural number. In the case of adding the surface-crosslinking agent two or more times, the particulate dried polymer that comes into contact with at least the surface-crosslinking agent at the first addition preferably has the above-described moisture content and temperature, and more preferably has the above moisture content and temperature at all points of contact. For each addition treatment, the same adding device may be used, or different devices may be used.

[2-6-2] Heat Treatment Step

The step is a step of heating the mixture of the particulate dried polymer and the surface-crosslinking agent to obtain a surface-crosslinked particulate dried polymer.

(Surface-Crosslinking Temperature)

In this step, a surface-crosslinked particulate dried polymer is obtained by heating the mixture of the particulate dried polymer and the surface-crosslinking agent to 100° C. or higher. The heating temperature (surface-crosslinking temperature) is selected as appropriate on the basis of the type of the surface-crosslinking agent to be added, but, from the viewpoint of the heat treatment efficiency, the heating temperature (surface-crosslinking temperature) is preferably 100° C. to 250° C., more preferably 120° C. to 230° C., and further preferably 150° C. to 210° C.

(Heating Time)

The time of heating the particulate dried polymer containing the surface-crosslinking agent at the surface-crosslinking temperature is set as appropriate in accordance with the moisture content of the particulate dried polymer, the type of the surface-crosslinking agent, operating conditions of the later-described heating device, and the like. As a rough standard, heating only needs to be performed until the moisture content of the obtained water-absorbent resin particles becomes 10% by mass or less, and the time is within a range of 10 minutes to 120 minutes and preferably 30 minutes to 90 minutes.

(Heating Device)

The production method according to the present invention is characterized by heating the mixture of the particulate dried polymer and the surface-crosslinking agent, using a heating device having a specific structure, in the surface-crosslinking step performed separately from the drying step. The heating device includes: a rotary container that contains the mixture of the particulate dried polymer and the surface-crosslinking agent therein and rotates; and a plurality of heating tubes that are located within the rotary container, extend in the axial direction of the rotary container, and rotate together with the rotary container. In the specification of the present application, the heating device having this configuration is sometimes referred to as "rotary heating device" or "rotary heating device with heating tubes".

In the rotary heating device, mainly by rotation of the rotary container and action of the plurality of heating tubes rotating together with the rotary container, the contents flow within the container, and thus mechanical and thermal damage to the particulate dried polymer is little. Accordingly, deterioration of physical properties and generation of fine powder in the surface-crosslinking step, particularly, in the heat treatment step are inhibited. Moreover, in the heating device, drying is performed by indirect heat transfer from the heating tubes, and thus there is an advantage that scattering as in hot air drying (a through-flow band drying machine or a through-flow heating type rotary kiln) does not occur and it is not necessary to treat a large volume of waste gas. Furthermore, in the heating device, by increasing the number of heating tubes, a heat transfer area within the heating device can be increased as compared to that of a conventionally used paddle dryer. The large heat transfer area enables heat treatment in a short time and also shortens the retention time within the device, thereby further reducing thermal damage.

Unless the objects of the present invention are disturbed, the rotary heating device may further include another heating means or thermal insulating means. From the viewpoint of heat treatment efficiency and reduction in thermal damage, direct heat transfer achieved by convection heat transfer and/or indirect heat transfer achieved by heat conduction from a heating surface (a contact surface with the particulate dried polymer containing the surface-crosslinking agent, a heat source portion) of the heating device heated by a heat medium is preferable as the other heating means or thermal insulating means. The heating means or thermal insulating means is more preferably of a through-flow heating type in the case of direct heat transfer and of an outer wall heating type in the case of indirect heat transfer.

Preferably, the heating device includes a heating means or a thermal insulating means on the outer peripheral surface of the rotary container. In the heating device, the particulate dried polymer and the surface-crosslinking agent contained in the rotary container are stirred and uniformly mixed by rotation of the rotary container, and the mixture thereof is heated by contact with the plurality of heating tubes or heat conduction from the heating tubes. The inner surface of the rotary container is also heated by radiant heat of the plurality of heating tubes and the like, and the particulate dried polymer mixed with the surface-crosslinking agent is further heated, as necessary, by the heating means or thermal insulating means located on the outer peripheral surface of the rotary container.

Unless the objects of the present invention are disturbed, the heating device may include another flowing means for causing the contents to flow. Examples of the other flowing means include a scooping plate, a stirring blade, and the like provided on the inner surface of the rotary container.

Preferably, the heating device has a function to introduce a gas into the device (preferably a means for introducing and discharging the gas). Examples of the means for introducing and discharging the gas include a gas introduction port and a gas discharge port. The numbers of gas introduction ports and gas discharge ports and the positions at which the gas introduction ports and the gas discharge ports are provided are not limited, the gas introduction ports and the gas discharge ports are preferably provided at the particulate dried polymer inlet side and outlet side of the heating device, and a gas introduction mechanism and a gas discharge mechanism may be provided as necessary. The gas is not particularly limited, but examples thereof include air, nitrogen, steam, mixed gases thereof, and the like. The gas serves as a carrier gas and promotes a crosslinking reaction by discharging steam or the like generated during heating to the outside of the device. Moreover, in the case of using a heated gas, the gas also serves as a heat medium and rapidly raises the temperature of the particulate dried polymer containing the surface-crosslinking agent to the above-described surface-crosslinking temperature. Preferably, nitrogen, steam, mixed gases thereof with air, and the like are used. In the case of using a mixed gas containing steam (hereinafter, also referred to as a high-humidity mixed gas), the interior of the device is brought into a low oxygen state, and oxidation or degradation during heating is inhibited. As a result, performance improvement and reduced coloring of the water-absorbent resin can be achieved.

The amount of the gas to be introduced, with respect to the processing amount per unit time (kg/hr) of the dried polymer in terms of solid content, is normally 0.01 to 3 $Nm^3/kg$, but is preferably 0.1 to 2 $Nm^3/kg$, more preferably 0.1 to 1 $Nm^3/kg$, and further preferably 0.3 to 0.5 $Nm^3/kg$.

In the heat treatment step, by introducing the gas into the heating device through one location or a plurality of locations, the dew point of the atmosphere within the heating device may be adjusted. The dew point of the atmosphere is preferably adjusted as appropriate in accordance with the moisture content of the particulate dried polymer to be put into the heating device and containing the surface-crosslinking agent. The dew point of the atmosphere is measured at the point of discharge from the heating device, and is preferably not lower than 60° C., more preferably not lower than 65° C., and further preferably not lower than 70° C. The upper limit of the dew point is not particularly limited, but the dew point is preferably not higher than 100° C. By setting the dew point within the above range, a crosslinking reaction is promoted, and the moisture content of the obtained water-absorbent resin particle is adjusted within a predetermined range, so that the fluid retention performance improves.

The movement direction of the gas in the heating device may be a parallel or counter flow direction with respect to the movement direction of the particulate dried polymer contained in the rotary container and containing the surface-crosslinking agent, or may be a mixture thereof.

The rotary heating device can also have a function to bring the device interior into a pressurized state, a normal pressure state, or a reduced pressure state. In the case of bringing the device interior into a pressurized state, the device interior is adjusted, for example, by increasing the amount of a carrier gas to be introduced into the heating device. The degree of pressurization with respect to the atmospheric pressure is preferably slight pressurization of greater than 0 kPa and not greater than 0.01 kPa. In the case of bringing the device interior into a reduced pressure state, the device interior is adjusted, for example, by changing the amount of exhaust gas (a carrier gas to be introduced, steam and the like generated during heat treatment) sucked from the heating device. The degree of pressure reduction with respect to the atmospheric pressure is slight pressure reduction of preferably greater than 0 kPa and not greater than 5 kPa, more preferably greater than 0 kPa and not greater than 2 kPa, and further preferably 0.01 to 0.5 kPa. By setting the degree of pressure reduction within the above range, steam and the like generated during heat treatment can be efficiently removed without taking an excessive amount of heat within the heating device, and thus the treatment time is shortened. In addition, aggregation and agglomeration of the water-absorbent resin particles in the heat treatment step is reduced. The term "degree of pressurization with respect to the atmospheric pressure" and the term "degree of pressure reduction with respect to the atmospheric pressure" mean differential pressures with respect to the atmospheric pressure and are represented as the absolute values of differences from the atmospheric pressure. For example, when the atmospheric pressure is the standard atmospheric pressure (101.3 kPa) and the degree of pressure reduction with respect to the atmospheric pressure is 10 kPa, the actual air pressure is 91.3 kPa.

In the production method according to the present invention, the above-described surface-crosslinking temperature is also adjusted on the basis of the temperature of a heat medium to be used in the heating device. For example, in the case where the aforementioned gas (hot air) is introduced into the heating device (mainly, a portion where the particulate dried polymer containing the surface-crosslinking agent is contained), the gas serves as a heat medium for direct heat transfer. From the viewpoint of heating efficiency by direct heat transfer, the temperature of the heat medium (gas) is preferably not lower than 100° C., more preferably not lower than 120° C., and further preferably not lower than 150° C.

In the case where the aforementioned heated gas (hot air) is introduced into the heating tubes of the heating device or the heating means or thermal insulating means (for example, a jacket or the like) provided on the outer surface of the heating device, the gas serves as a heat medium for indirect heat transfer. From the viewpoint of heating efficiency by indirect heat transfer, the temperature of the heat medium (gas) is preferably not lower than 100° C., more preferably not lower than 120° C., further preferably not lower than 150° C., and particularly preferably not lower than 180° C. If the temperature of the heat medium is lower than 100° C., the progress of the crosslinking reaction in the surface treatment becomes slow. In the case of indirect heat transfer, a heat medium in liquid form such as oil may be used as a heat medium other than gas, but steam is preferable. As long as the objects of the present invention are achieved, the temperature of the heated gas (hot air) to be introduced into the plurality of heating tubes is not particularly limited. However, from the viewpoint of heating efficiency, the temperatures of the heated gas at all the heating tubes may be equal or may be different, but are normally equal. In the case where the temperatures of the heated gas are different, the temperature is specified as the average of these temperatures.

In the production method according to the present invention, from the viewpoint of stirring efficiency, the Froude number ($Fr=\omega^2 \cdot r/g$) of the rotary heating device is set as appropriate on the basis of the device size or the processing amount per unit time, but is within a range of preferably 0.001 to 1, more preferably 0.005 to 0.5, further preferably 0.01 to 0.3, and particularly preferably 0.02 to 0.2. The Froude number Fr is the ratio of centrifugal acceleration $\omega^2 \cdot r$ applied to the contents stirred within the rotary container, relative to gravitational acceleration g. $\omega$ is the angular velocity of a rotator [rad/sec], and r is a representative radius of the rotator [m].

The rotation speed of the rotary container is set as appropriate on the basis of the device size or the processing amount per unit time, but is preferably 1 rpm to 250 rpm, more preferably 1 rpm to 100 rpm, and further preferably 2 rpm to 50 rpm. In addition, the maximum peripheral speed of the rotary container is not particularly limited, but is preferably 0.05 m/s to 10 m/s, more preferably 0.1 m/s to 8 m/s, and further preferably 0.15 m/s to 5 m/s.

The filling rate in the rotary heating device (the ratio of the filled volume ($m^3$) of the contents to the effective capacity ($m^3$) of the rotary container) is selected as appropriate, but is within a range of preferably 5% to 95%, more preferably 6% to 50%, and further preferably 10% to 40%, from the viewpoint of heat treatment efficiency.

In the production method according to the present invention, in order to efficiently transfer heat to the contents of the rotary container, a heating device having a large heat transfer area with respect to an internal capacity thereof is preferable. The heat transfer area with respect to the internal capacity is defined as the ratio (heat transfer area/effective capacity) of the heat transfer area ($m^2$) to the effective capacity ($m^3$) of the rotary container. When the ratio is higher, the efficiency of heat transfer improves, and the rate of temperature rise of the contents increases. As a result, the heating time is shortened, thus thermal and mechanical damage is reduced, and the productivity improves. The ratio is set as appropriate on the basis of the specifications and the type of the heating device, the form of the contents, and the like, but is preferably not less than 10 $m^{-1}$, more preferably not less than 12 $m^{-1}$, and further preferably not less than 15 $m^{-1}$. The effective capacity is the inner capacity of the rotary container in which the contents are contained, and the heat transfer area means the area of a heating surface that can provide heat to the contents contained in the rotary container. Specifically, the sum of the areas of the outer peripheral surfaces of the plurality of heating tubes and the area of the inner peripheral surface of the rotary container in the case of heating the outer surface of the rotary container is the heat transfer area.

Figure 2:
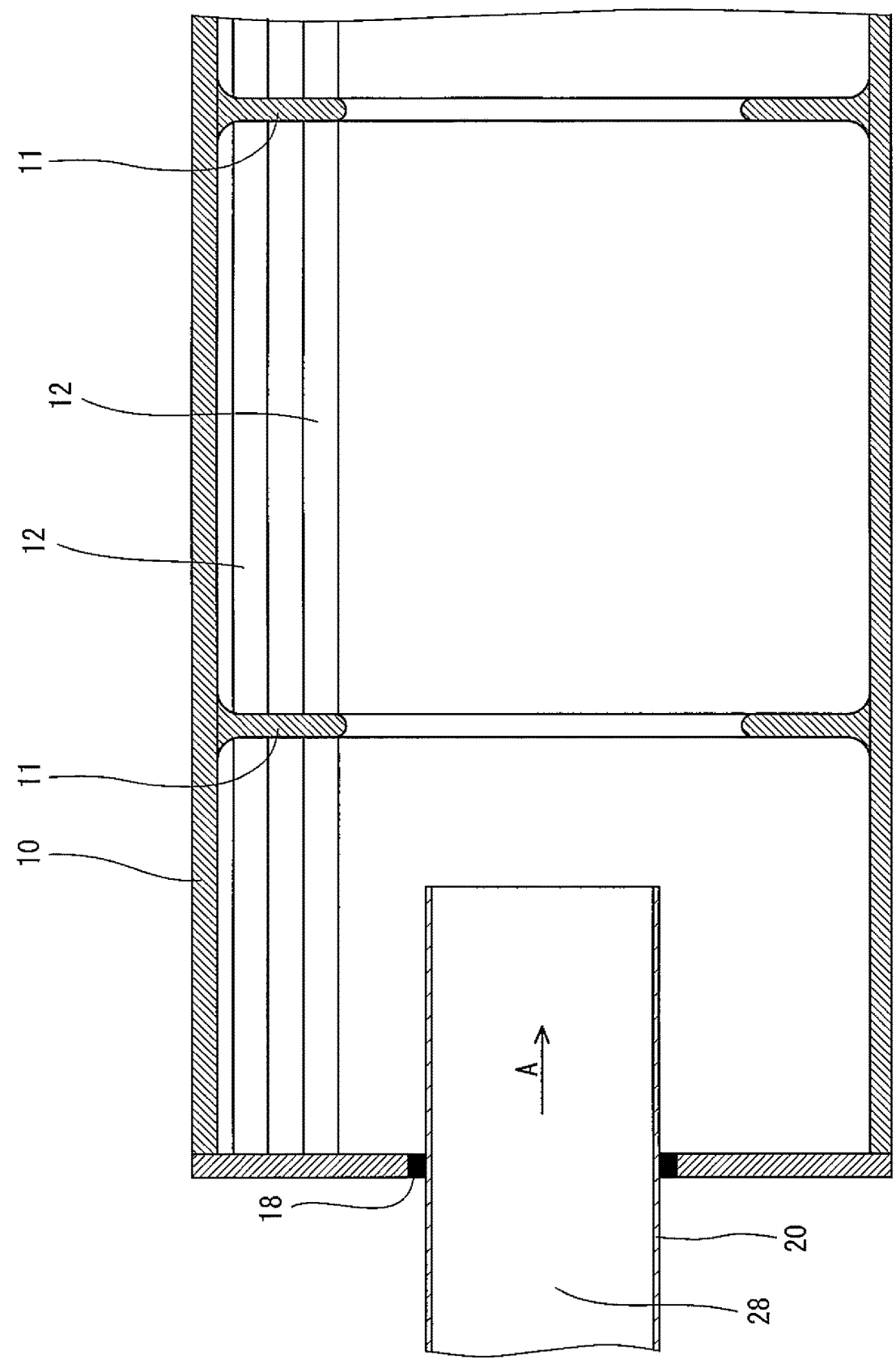
FIG. 2 is an enlarged cross-sectional view showing a part of the heating device in FIG. 1.

FIGS. 1 and 2 show an example of a rotary heating device 100 with heating tubes. The following will describe an example of a basic configuration and a use method of the rotary heating device 100 with heating tubes with reference to FIGS. 1 and 2.

As shown, the heating device 100 has a main portion 4, an input portion 6, and a takeout portion 8. The main portion 4 has a rotary container 10, a plurality of heating tubes 12, a first gear 14, a second gear 16, and a packing 18. The rotary container 10 generally has a cylindrical shape. The right-left direction in FIG. 1 is the axial direction of the rotary container 10. A plurality of obstructive walls 11 are provided on the inner wall of the rotary container 10 so as to be spaced apart from each other in the axial direction. Each of the obstructive walls 11 extends along the inner peripheral surface of the rotary container 10.

The plurality of heating tubes 12 are housed within the rotary container 10. Each of the heating tubes 12 extends in the axial direction of the rotary container 10 and penetrates both ends of the rotary container 10. None of the plurality of heating tubes 12 is in contact with the inner peripheral surface of the rotary container 10 in the axial direction.

In FIG. 2, for the convenience of explanation, merely some of the heating tubes 12 are shown. The first gear 14 is fixed to the outer peripheral surface of the rotary container 10. The second gear 16 is in mesh with the first gear 14. In FIG. 2, for the convenience of explanation, the first gear 14 and the second gear 16 are not shown. The packing 18 is located between the rotary container 10 and the input portion 6.

The input portion 6 has a main tube 20 and a hopper 22. As shown in FIG. 2, the main tube 20 is open within the rotary container 10. The interior of the main tube 20 is referred to as an inner space 28. The hopper 22 has a shape in which the inner dimension thereof gradually decreases from the upper side toward the lower side. The lower end of the hopper 22 is fixed to the main tube 20. Although not shown, the hopper 22 communicates with the inner space 28.

The takeout portion 8 has a takeout port 40, a steam inlet 44, and a drain 46. The steam inlet 44 communicates with the plurality of heating tubes 12. The drain 46 also communicates with the plurality of heating tubes 12.

Figure 3:
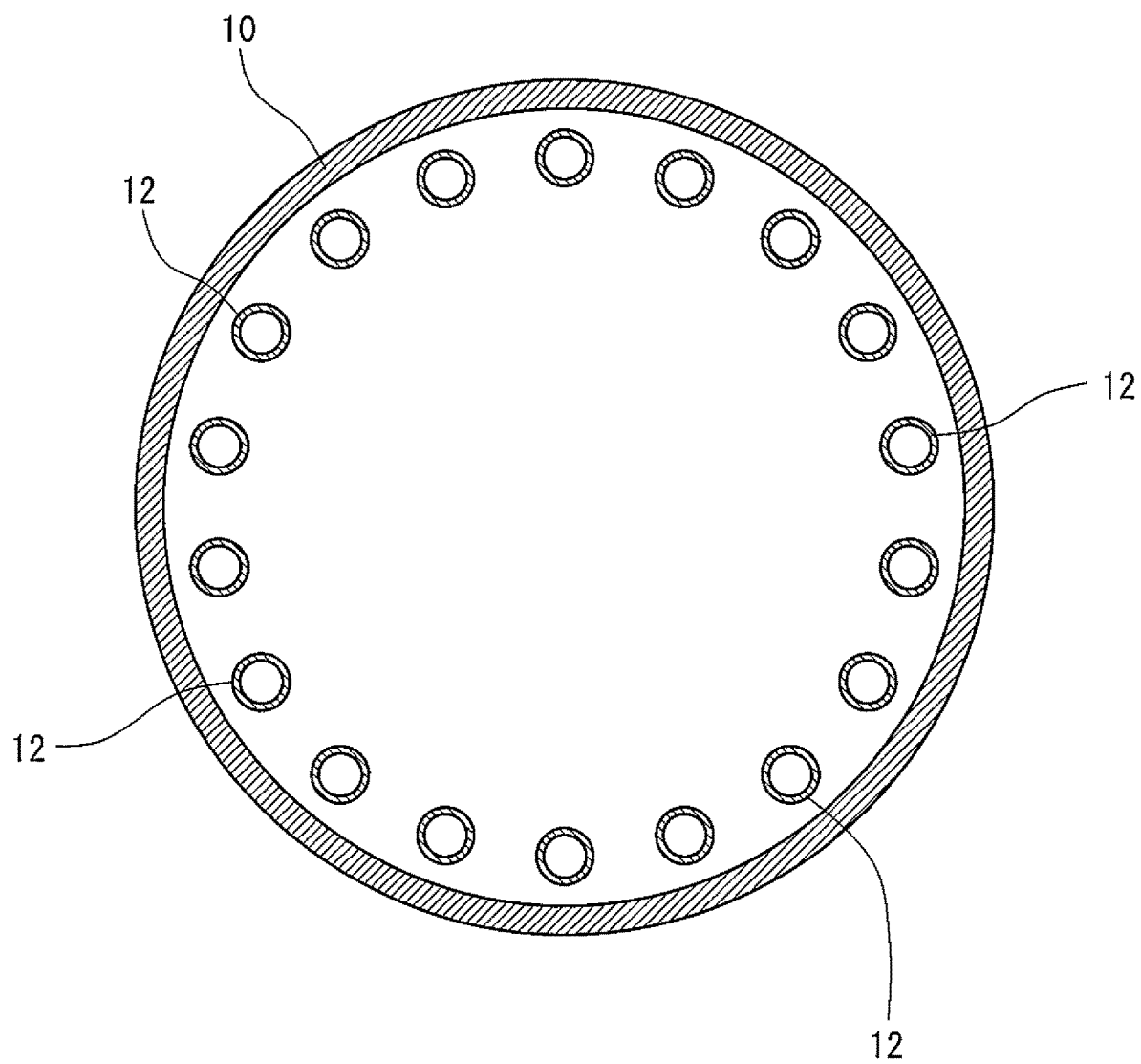
FIG. 3 is a cross-sectional view of the heating device taken along a line III-III in FIG. 1.

FIG. 3 is a cross-sectional view of the heating device 100 taken along a line III-III in FIG. 2. As shown, the heating device 100 of this embodiment has 18 heating tubes 12. These heating tubes 12 are arranged on a concentric circle centered on the rotation axis of the rotary container 10, so as to be spaced apart from each other. When the inner radius (radius) of the rotary container 10 is denoted by R and the length in the axial direction of the rotary container 10 is denoted by L, the inner peripheral surface area of the rotary container 10 is $2\pi RL$. Meanwhile, when the outer radius (radius) of each heating tube 12 is denoted by r and the length in the axial direction of each heating tube 12 is denoted by l, the total area of the outer peripheral surfaces of the 18 heating tubes 12 is $36\pi rl$. The outer radius r of each heating tube 12 is sufficiently small with respect to the inner radius R of the rotary container 10, and the length l in the axial direction of each heating tube 12 and the length L in the axial direction of the rotary container 10 are normally approximate to each other. Therefore, the heat transfer area of the 18 heating tubes 12 is larger than the inner peripheral surface area of the rotary container 10. With the heating device 100, it is possible to perform efficient heat treatment since the 18 heating tubes 12 have a heat transfer surface wider than the inner peripheral surface area of the rotary container 10.

To allow the heat treatment step to be performed by the heating device 100, steam is introduced through the steam inlet 44 toward the heating tubes 12. The temperature within the rotary container 10 is increased by the steam. A part of the steam is cooled by heat exchange. The cooled steam turns to water and is discharged through the drain 46. The temperature within the rotary container 10 is controlled by continuously introducing steam through the steam inlet 44 so as to make up for the steam that has turned to water and been discharged.

A gas is introduced into the rotary container 10. The gas fills the interior of the rotary container 10. Excess gas is discharged from the rotary container 10.

The second gear 16 is rotated by a drive means (for example, a motor) that is not shown. By the rotation of the second gear 16, the first gear 14 rotates, and the rotary container 10 further rotates. The plurality of heating tubes 12 also rotate together with the rotary container 10. The input portion 6 is cut off from the rotary container 10 by the packing 18. Thus, even when the rotary container 10 rotates, the input portion 6 does not rotate. Similarly, even when the rotary container 10 rotates, the takeout portion 8 does not rotate.

After the gas in the rotary container 10 reaches a predetermined temperature, a particulate dried polymer containing a surface-crosslinking agent is put into the hopper 22. The particulate dried polymer containing the surface-crosslinking agent advances in the inner space 28 toward the direction indicated by an arrow A in FIG. 2. The particulate dried polymer containing the surface-crosslinking agent is introduced into the rotary container 10. The particulate dried polymer containing the surface-crosslinking agent is stirred and mixed by rotation of the rotary container 10 and action of the plurality of heating tubes 12 rotating together with the rotary container 10. Furthermore, the particulate dried polymer containing the surface-crosslinking agent is heated by heat exchange with steam passing through the heating tubes 12 and the gas introduced into the rotary container 10, and the temperature of the particulate dried polymer is raised to the surface-crosslinking temperature. By the heating and stirring by the heating device 100, a crosslinking reaction proceeds, and the particulate dried polymer containing the surface-crosslinking agent is adjusted to a predetermined moisture content.

Although not shown, the heating device 100 is provided with an inclination in the axial direction from one end thereof toward the other end thereof. In the heating device 100, a downward inclination is provided from the input portion 6 toward the takeout portion 8. Due to the inclination and rotation of the rotary container 10, the particulate dried polymer containing the surface-crosslinking agent gradually advances within the rotary container 10 in the rightward direction in FIG. 1, that is, from the input portion 6 toward the takeout portion 8, while being heated and stirred.

In the advancement direction of the particulate dried polymer containing the surface-crosslinking agent, the obstructive walls 11 are present. By the obstructive walls 11, mixing of particulate dried polymers having different surface-crosslinked states and different moisture contents within the rotary container 10 is avoided, so that piston flowability improves. Accordingly, surface crosslinking is substantially uniformly achieved, and a high-quality particulate dried polymer adjusted to a predetermined moisture content is obtained. The surface-crosslinked particulate dried polymer is taken out through the takeout port 40.

As described above, none of the plurality of heating tubes 12 is in contact with the inner peripheral surface of the rotary container 10 in the axial direction. As shown in FIG. 3, the plurality of heating tubes 12 are provided near the inner peripheral surface of the rotary container 10 (at positions outward by preferably 50 to 99% and more preferably 60 to 95% of the radius of the rotary container 10) when being seen from the center (rotation axis) of the rotary container 10. The plurality of heating tubes 12 efficiently contact with the particulate dried polymer containing the surface-crosslinking agent. The particulate dried polymer containing the surface-crosslinking agent is stirred not only by rotation of the rotary container 10 but also by rotation of the heating tubes 12 that are synchronous with the rotation of the rotary container 10, and is heated by indirect heat transfer from the heating tubes 12 at the same time, whereby a crosslinking reaction proceeds. The rotary container 10 may have another heating mechanism, but the inner surface of the rotary container 10 is heated mainly by radiant heat from the heating tubes 12 or heat transfer from the particulate dried polymer, or also a heated gas in the case of introducing this gas.

In the heating device 100 according to the present invention, a heat medium having the aforementioned temperature (preferably not lower than 100° C.) is preferably introduced into the plurality of heating tubes 12. From the viewpoint of reduction in adhesion in the heat treatment step, the inner surface of the rotary container 10 is more preferably also heated to a predetermined temperature by radiant heat from the heating tubes 12, or by a heated gas in some cases. From the viewpoint of promotion of a crosslinking reaction, the temperature of the inner surface of the rotary container 10 is preferably not lower than 100° C., more preferably not lower than 120° C., further preferably not lower than 150° C., and particularly preferably not lower than 180° C. The upper limit of the temperature of the inner surface of the rotary container 10 is normally equal to the temperature of the heating tubes 12. The temperature of the inner surface of the rotary container 10 is measured, for example, by one or more thermometers provided to the heating device 100 for material temperature measurement.

Furthermore, also in the case of introducing a gas into the rotary container 10, the inner surface of the rotary container 10 is heated to the aforementioned temperature mainly by radiant heat from the heating tubes 12. From this viewpoint, the temperature of the gas is preferably not lower than 100° C. and more preferably not lower than 120° C. The temperature of the inner surface of the rotary container 10 is preferably higher than the temperature of the gas by +10° C. or higher, further preferably +20° C. or higher, and particularly preferably +30° C. or higher.

Moreover, before the particulate dried polymer containing the surface-crosslinking agent is put into the rotary container 10, the temperature of the inner surface of the rotary container 10 is preferably heated to a temperature within the above range (preferably not lower than 100° C.). Accordingly, adhesion of the particulate dried polymer containing the surface-crosslinking agent to the inner surface of the rotary container 10 and the heating tubes 12 is reduced, and a reduction in treatment efficiency caused by adhesion to the heating tubes 12 is also avoided. Thus, such heating is preferable. That is, in the surface-crosslinking method according to the present invention, before the particulate dried polymer containing the surface-crosslinking agent is put inside, the inner surface of the rotary container 10 is preferably heated to the predetermined temperature or higher. The above phenomenon is observed during heat treatment of a particulate dried polymer having a moisture content increased by addition of the surface-crosslinking agent, and it is necessary to take into consideration the temperature of the inner surface of the rotary container 10 at the start of heat treatment of the particulate dried polymer containing the surface-crosslinking agent (Start-up).

In the production method according to the present invention, the number, the arrangement, and the shapes of the obstructive walls 11 (also referred to as partition plates) included in the heating device 100, and the number of openings in each obstructive wall 11 are not particularly limited, and the shape of each obstructive wall 11 is selected as appropriate from a donut shape, a semi-donut shape, a ⅓ to ¹/₁₀ donut shape, a semi-circular shape (½ circle shape), a ⅓ to ¹/₁₀ circle shape, a crescent shape, and the like in accordance with the particulate dried polymer to be supplied to the heating device 100 and containing the surface-crosslinking agent and the physical properties of water-absorbent resin particles to be obtained. Typically, obstructive walls 11 each having a donut shape can be used, but the obstructive walls 11 are not particularly limited thereto. The number of openings in each obstructive wall 11 only needs to be one or more. In the case where each obstructive wall 11 has a plurality of openings, the sizes of the openings may be the same or different from each other. Each obstructive wall 11 may have one or more openings for discharging to the outside. A preferable opening ratio will be described later. The obstructive walls 11 may be provided so as to be perpendicular to a cross-section of the rotary container 10, or may be inclined relative thereto.

Figure 5:
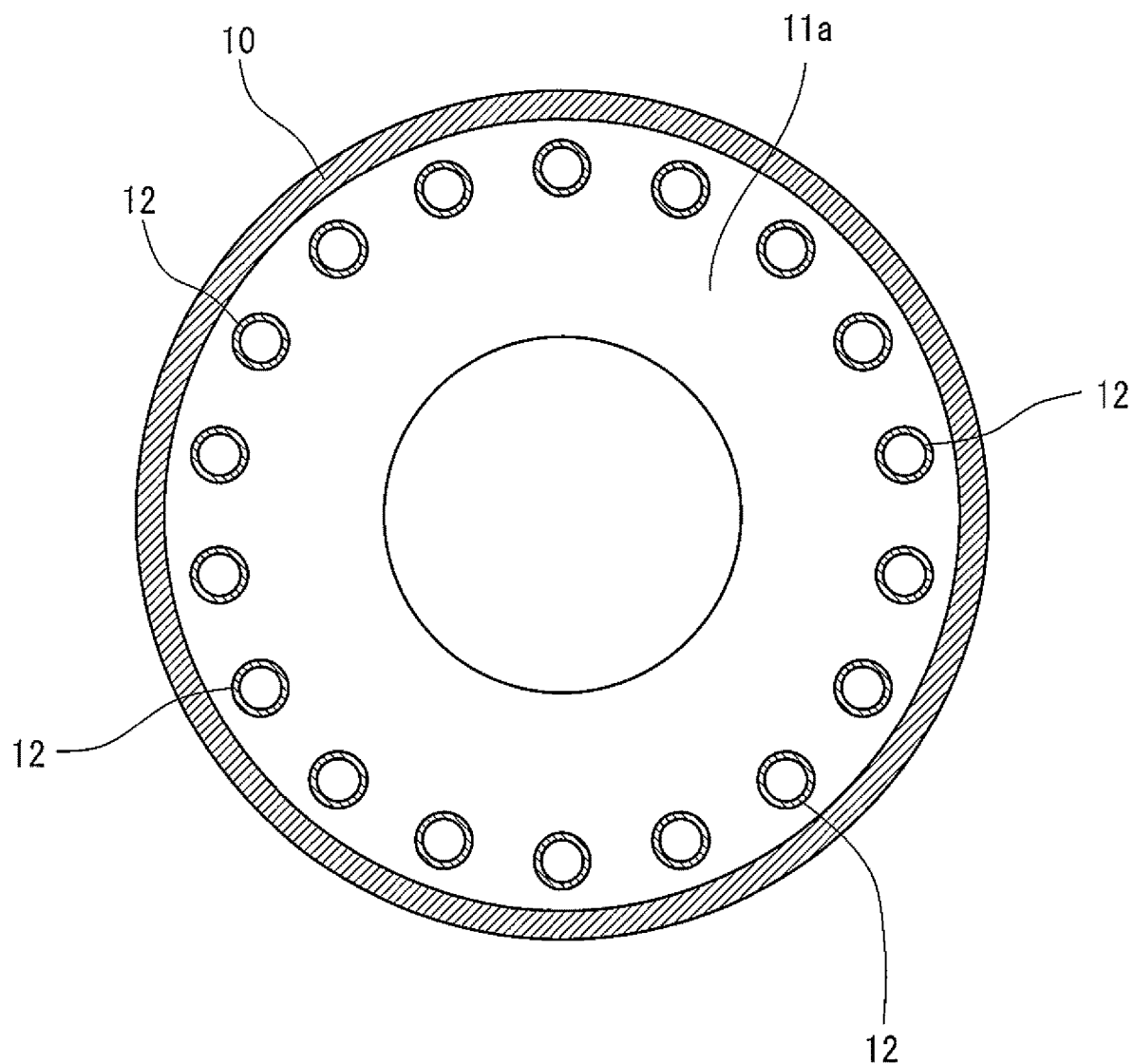
FIG. 5 shows an example of a shield having an opening (opening ratio: 20%) used in a heating device (rotary heating device with heating tubes) used in the production method according to the present invention.
Figure 6:
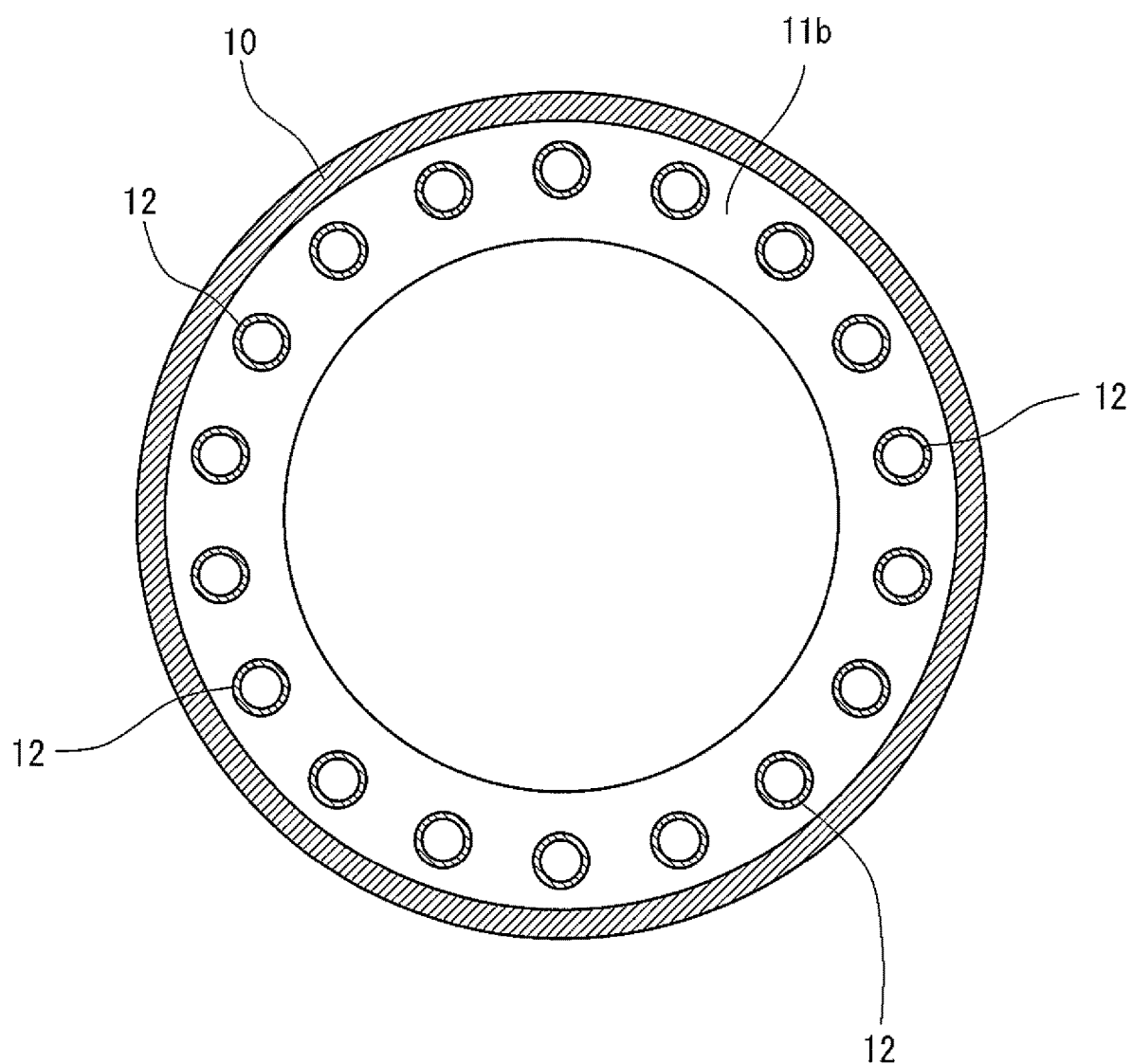
FIG. 6 shows an example of a shield having an opening (opening ratio: 50%) used in a heating device (rotary heating device with heating tubes) used in the production method according to the present invention.
Figure 7:
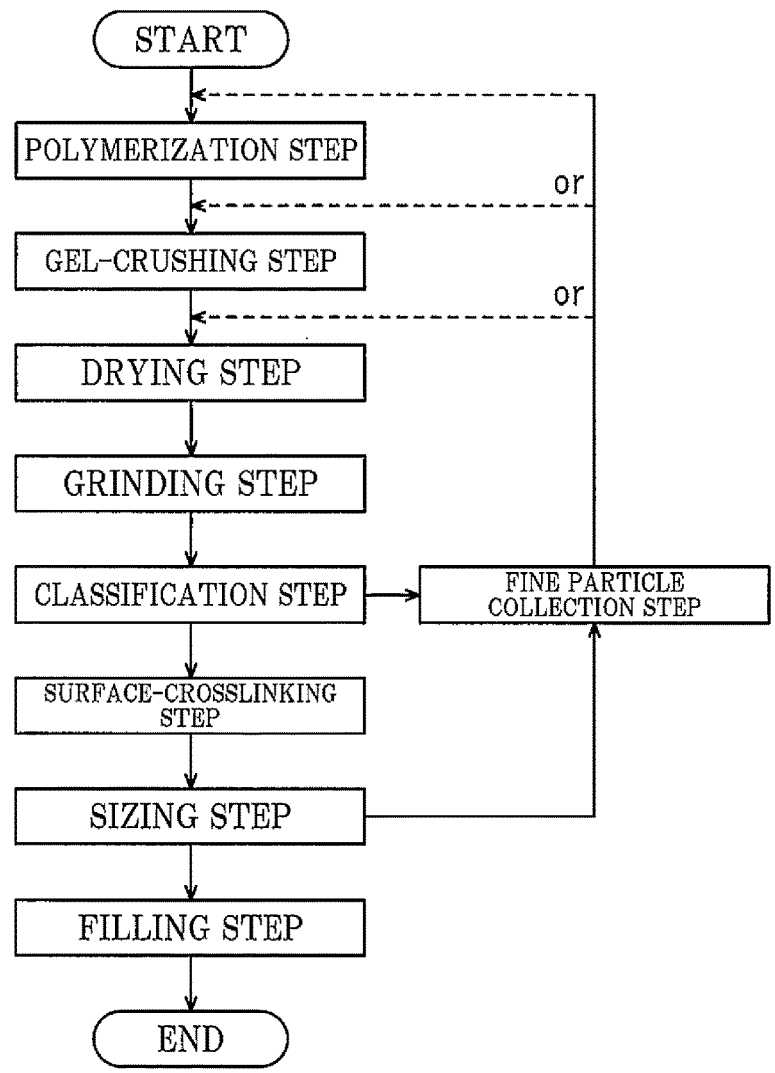
FIG. 7 is a flowchart for explaining a typical production method for a water-absorbent resin.

The shapes of typical obstructive walls 11 are shown in FIGS. 5 and 6. An obstructive wall 11a in FIG. 5 and an obstructive wall 11b in FIG. 6 are each a donut-shaped partition plate that is provided so as to be orthogonal to the axial direction of the cylindrical rotary container 10 and has an opening in a substantially center portion.

The opening ratio of each obstructive wall 11 (the ratio of the opening in the obstructive wall 11 with respect to the cross-sectional area perpendicular to the axial direction of the rotary container 10) is determined as appropriate regardless of the shape of the obstructive wall 11, but is normally 1 to 90%, preferably 2 to 50%, more preferably 5 to 45%, and further preferably 10 to 40%. If the opening ratio is greater than the aforementioned range, the effect exhibited by the obstructive wall 11 is low. If the opening ratio is less than the aforementioned range, a discharge failure may occur. The opening ratio of the obstructive wall 11a in FIG. 5 is 20%, and the opening ratio of the obstructive wall 11b in FIG. 6 is 50%.

From the viewpoint of heating efficiency and piston flowability, the number (n) of obstructive walls 11 is at least one, preferably not less than two, and particularly preferably not less than three. The upper limit of the number of obstructive walls 11 depends on the size of the heating device 100, but the number of obstructive walls 11 is preferably not greater than 20 and more preferably not greater than 10.

Figure 4:
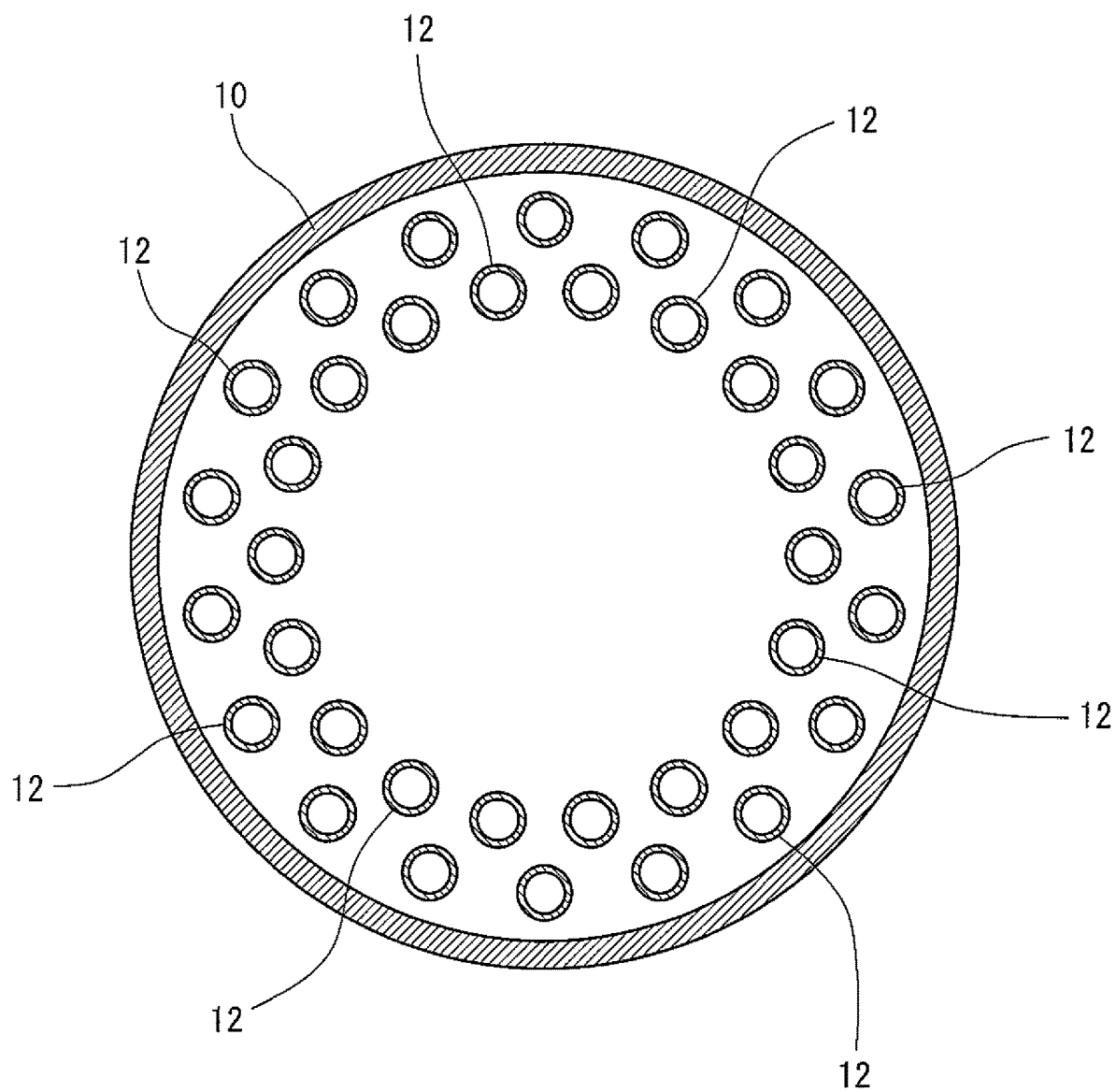
FIG. 4 is a cross-sectional view for explaining a heating device (rotary heating device with heating tubes in two layers) used in the production method according to the present invention.

In the production method according to the present invention, the arrangement of the heating tubes 12 included in the heating device 100 is not particularly limited, and is set as appropriate in accordance with a quantity of production, etc. As shown in FIG. 3, the plurality of heating tubes 12 may be arranged on the circumference of a circle centered on the rotation axis of the rotary container 10, so as to be spaced apart from each other, or may be arranged on two or more (multiple) concentric circles centered on the rotation axis of the rotary container 10, so as to be spaced apart from each other, as shown in FIG. 4. In addition, the plurality of heating tubes 12 may be arranged radially from the rotation axis of the rotary container 10 toward the outer side in the radial direction so as to be spaced apart from each other. In the case of arranging the plurality of heating tubes 12 in multiple layers along a circumference, the number of layers is selected in accordance with the purpose, but the heating tubes 12 are arranged preferably in 2 layers to 10 layers, more preferably in 2 layers to 8 layers, and further preferably in 2 layers to 5 layers. When the heating tubes 12 are arranged in multiple layers, a wider heat transfer surface is provided, and thus it is possible to perform more efficient heat treatment.

In the production method according to the present invention, the number and the radii (diameters) of the heating tubes 12 included in the heating device 100 are also not particularly limited. From the viewpoint of heating efficiency, the number of the heating tubes 12 is determined as appropriate on the basis of the size or the processing amount of the heating device 100, but is preferably not less than 5, more preferably not less than 10, further preferably not less than 15, even further preferably not less than 20, and particularly preferably not less than 100. The upper limit of the number of the heating tubes 12 is not particularly limited, but, for example, 2000 or less and further 1000 or less are selected as appropriate. The area of a heating surface that is in contact with a material in indirect heating is increased by the multiple heating tubes 12, which is preferable.

In the heating device 100, the inner surface of the rotary container 10 is heated by radiant heat from the heating tubes 12 or heat transfer from the contents. From the viewpoint of preventing adhesion or aggregation of the particulate dried polymer during progress of the crosslinking reaction, the heating device 100 further includes, preferably, a heating means or a thermal insulating means, and more preferably a heating means, on the outer peripheral surface of the rotary container 10. An example of the thermal insulating means is a technique in which a part or the entirety of the outer peripheral surface of the rotary container 10 (preferably not less than 50%, more preferably not less than 80%, and particularly preferably the entirety of the outer peripheral surface of the rotary container 10) is covered with a thermal insulator. In addition, examples of the heating means include an electric trace, a steam trace, a jacket heated by a heat medium, and the like. In the production method according to the present invention, from the viewpoint of reduction in aggregation of the particulate dried polymer containing the surface-crosslinking agent, not only the temperature of the heating tubes 12 but also control of the temperature of the inner surface of the rotary container 10 is important at the start of heat treatment (Start-up). The heating means or the thermal insulating means provided on the outer surface of the rotary container 10 is effective for controlling the temperature of the inner surface of the rotary container 10.

(Additives)

Unless the advantageous effects of the present invention are impaired, in the heating device 100, other additives may be added to the particulate dried polymer containing the surface-crosslinking agent. Examples of the other additives include the above-described gel fluidizer and polymer lubricant.

(Quantity of Production)

In the production method according to the present invention, by using the heating device 100 having the basic configuration shown in FIGS. 1 and 2 in the heat treatment step of the surface-crosslinking step, it is possible to perform continuous treatment with the processing amount per unit time (kg/hr) in terms of solid content of the water-absorbent resin being not less than 7 Kg/hr, preferably not less than 50 Kg/hr, more preferably not less than 100 Kg/hr, and particularly preferably not less than 500 Kg/hr. The continuous treatment time is preferably not shorter than 12 hours, more preferably not shorter than 24 hours, further preferably not shorter than 240 hours, and particularly preferably not shorter than 1200 hours.

Examples of the heating device described above include rotary drying machines with steam tubes. Specific examples thereof include a steam tube dryer (manufactured by Kurimoto, Ltd.), a steam tube dryer (manufactured by Ube Machinery Corporation, Ltd.), a steam tube dryer (manufactured by Tsukishima Kikai Co., Ltd.), a steam tube dryer (manufactured by Mitsui Engineering & Shipbuilding Co., Ltd.), and the like.

As long as the objects of the present invention are achieved, the number of rotary heating devices that can be used in the heat treatment step may be only one, or may be a plural number that is two or more. A plurality of rotary heating devices having different specifications may be used in combination. As long as the rotary heating device is used in the heat treatment step of the first surface-crosslinking step performed separately from the polymerization step, it is also possible to subsequently perform additional heat treatment by using another heating device that is not classified as a rotary heating device. In this case, the type and number of heating devices used for the additional heat treatment are not limited.

Examples of the other heating device that is not classified as the heating device used in the production method according to the present invention (that is, a rotary heating device) include a single-shaft or twin-shaft disc drying machine, a single-shaft or twin-shaft paddle drying machine, a rotary dryer, a rotary kiln, and the like. Specifically, such as Solidair (manufactured by HOSOKAWA MICRON CORPORATION), a CD dryer (manufactured by Kurimoto, Ltd.), a paddle dryer (manufactured by NARA MACHINERY CO., LTD.), a rotary kiln (manufactured by Kurimoto, Ltd.), a rotary dryer (manufactured by OKAWARA MFG. CO., LTD.), and the like, can be optionally used.

[2-7] Cooling Step

Preferably, a cooling step of forcedly cooling the dried polymer or the surface-crosslinked particulate dried polymer to adjust the dried polymer or the surface-crosslinked particulate dried polymer to a desired temperature, after the above-described drying step and/or heat treatment step and before a later-described sizing step, is included. For example, in the case where the surface-crosslinking step is carried out in the above-described heating device 100 separately from the drying step, the cooling step is carried out in the rotary container 10 before surface-crosslinking treatment is appropriately performed and the particulate dried polymer adjusted to a desired moisture content or solid content rate is subjected to the sizing step. In addition, the cooling step is carried out before the dried polymer adjusted to a desired moisture content or solid content rate in the drying step is subjected to the sizing step prior to the surface-crosslinking step.

Specifically, with respect to a temperature t° C. of the dried polymer and/or the surface-crosslinked particulate dried polymer, the dried polymer and/or the surface-crosslinked particulate dried polymer is forcedly cooled to preferably (t−20°) C. or lower, more preferably (t−30°) C. or lower, and further preferably (t−40°) C. or lower. For example, in the case where the temperature t of the dried polymer and/or the surface-crosslinked particulate dried polymer is 150° C. to 250° C., the dried polymer and/or the surface-crosslinked particulate dried polymer is forcedly cooled to preferably 50° C. to 130° C., more preferably 60° C. to 100° C., and further preferably 65° C. to 90° C. before being subjected to the sizing step. By cooling to a temperature within this range, the workability at the time of crushing and the accuracy of classification in the sizing step are improved, so that the physical properties of obtained water-absorbent resin particles are improved.

(Cooling Method)

The method for cooling the dried polymer or the surface-crosslinked particulate dried polymer in the cooling step is not particularly limited. A continuous cooling machine having a through-flow heat transfer type or conductive heat transfer type cooling means is preferably used. The dried polymer or the surface-crosslinked particulate dried polymer may be cooled in a state where the dried polymer or the surface-crosslinked particulate dried polymer is left at rest, or while being stirred. A material stirring type cooling machine is preferable, and a continuous material stirring type cooling machine is more preferable. For example, a fluidized bed cooling machine that employs direct heat transfer is exemplified. Cooling with cold air by a continuous belt type cooling machine may be performed.

Preferably, a stirring device having a rotary shaft can be used for stirring cooling. For example, a mixer having a function to allow air current to flow to an object to be cooled and cool the object is widely used as a cooling machine. As long as the advantageous effects of the present invention are achieved, the direction of the air current is not particularly limited, and may be the up-down direction or may be the right-left direction. Specific examples of such a cooling machine include devices that are used by causing air current to flow through a mixer having a horizontal rotary shaft and a container that rotates (a horizontal cylindrical type, an inclined cylindrical type, a V-shaped type, a double conical type, a cubic type, an S-shaped type, a continuous V-shaped type, etc.), a mixer having a horizontal rotary shaft and a fixed container (a ribbon type, a screw type, a conical screw type, a groove stirring type, a high speed flow type, a rotary disk type, a Muller type, a paddle type, a rotary type, a disk type, etc.), or the like. Preferably, a container fixed type cooling machine that has a rotary stirring blade for stirring water-absorbent resin powder that is an object to be cooled and allows air current to flow therein, is used. These cooling machines may be of a continuous type or may be of a batch type, but is preferably of a continuous type.

[2-8] Sizing Step

This step is a step of adjusting the particle size of the dried polymer and/or the surface-crosslinked particulate dried polymer. By subjecting the particulate dried polymer that has undergone the surface-crosslinking step to the sizing step, water-absorbent resin particles having a more positively controlled particle diameter or particle size distribution are obtained. In particular, for the surface-crosslinked particulate dried polymer obtained in the production method according to the present invention, since adhesion and aggregation of particles in the surface-crosslinking step is reduced, there is an advantage that the load in this step is low and the amount of fine powder generated due to excessive grinding or crushing is small. It is also possible to carry out this step a plurality of times.

[2-9] Fine Powder Recycling Step

The term "fine powder recycling step" means a step of supplying the fine powder removed in the classification step, to any step without changing the fine powder or after granulating the fine powder. The fine powder recycling step is preferably a step of putting fine powder or fine powder-granulated material into a step prior to the drying step and reusing the fine powder or fine powder-granulated material therein. Examples of putting into the step prior to the drying step include the monomer solution, before polymerization, that is prepared in the polymerization step, the hydrous gel during polymerization, and the crushing step for the hydrous gel after polymerization, the drying step for the particulate hydrous gel, and the like. To these steps, the fine powder may be added without changing the fine powder, or the fine powder may be added after being swollen into a gel by water or granulated. In addition, together with the fine powder, water, a crosslinking agent, a binder (for example, a water-soluble polymer, a thermoplastic resin) other than water, a polymerization initiator, a reducing agent, a chelating agent, a color protecting agent, and the like may be added. For example, in the case of adding water, the water is preferably used in an amount of 1% by mass to 1000% by mass with respect to the fine powder. In the case of adding another compound, the other compound is preferably used in an amount of 0.01% by mass to 10% by mass with respect to the fine powder.

With the production method according to the present invention, the amount of bulky particles in the obtained surface-crosslinked particulate dried polymer is small, the mechanical load in the sizing step is reduced, and the amount of fine powder is also reduced. Therefore, labor saving can be also achieved in a fine powder removing step and a fine powder collection step. As compared to mere removal of fine powder, collection and recycling of removed fine powder may cause a decrease in performance of a water-absorbing agent (for example, a decrease in water absorption capacity, re-generation of fine powder during a step, etc.). However, according to the present invention, since the amount of fine powder is reduced, a decrease in performance caused by collection and recycling of fine powder is also reduced, and the performance of the obtained water-absorbing agent improves. A preferable amount of fine powder collected is set as appropriate on the basis of a target particle size. In the case of producing water-absorbent resin particles having a small particle diameter, the amount of fine powder also tends to increase consequently, but the amount of fine powder is preferably less than 30% by mass, more preferably not greater than 20% by mass, further preferably not greater than 15% by mass, and particularly preferably not greater than 10% by mass, of the total quantity of production.

[2-10] Other Steps

In addition to the respective steps described above, the production method according to the present invention may further include a grinding step, a re-swelling step, a granulation step, a transport step, a storage step, a packing step, a keeping step, and the like as necessary.

(Other Additives)

Unless the advantageous effects of the present invention are impaired, it is possible to further add inorganic fine particles, a dust inhibitor, a dried water-absorbent resin (fine powder), a liquid permeability improver, and the like as other additives in addition to the above optionally used gel fluidizer and polymer lubricant.

Specific examples of the inorganic fine particles include: mineral products such as talc, kaolin, fuller's earth, hydrotalcite, bentonite, activated clay, barite, natural asphaltum, strontium ore, ilmenite, pearlite, and the like; aluminum compounds such as aluminum sulfate tetradeca- to octadecahydrates (or anhydrates thereof), potassium aluminum sulfate dodecahydrate, aluminum sodium sulfate dodecahydrate, aluminum ammonium sulfate dodecahydrate, aluminum chloride, polyaluminum chloride, aluminum oxide, and the like; other polyvalent metal salts, polyvalent metal oxides, and polyvalent metal hydroxides such as calcium phosphate and the like; hydrophilic amorphous silicas; oxide complexes such as complexes of silicon oxide, aluminum oxide, and magnesium oxide, complexes of silicon oxide and aluminum oxide, complexes of silicon oxide and magnesium oxide, and the like; and the like. Two or more of them may be used in combination.

[3] Physical Properties of Water-Absorbent Resin Particles as Product

Regarding the water-absorbent resin particles (water-absorbing agent) obtained by the production method according to the present invention, in the case where the water-absorbent resin particles are used for absorbent articles, particularly, for disposable diapers, among physical properties described below in (3-1) to (3-6), at least one, preferably two or more, more preferably three or more, and further preferably all the physical properties are desirably controlled within desired ranges. When all of the physical properties described below do not satisfy the ranges described below, the advantageous effects of the present invention are not sufficiently achieved, and sufficient performance may not be exerted particularly in so-called high-concentration disposable diapers in which the amount of the water-absorbing agent used per disposable diaper is large.

[3-1] CRC (Centrifuge Retention Capacity)

The CRC (centrifuge retention capacity) of the water-absorbent resin particles (water-absorbing agent) of the present invention is normally not less than 5 g/g, preferably not less than 15 g/g, and more preferably not less than 25 g/g. The upper limit thereof is not particularly limited, and a higher CRC is preferable. However, from the viewpoint of balance with the other physical properties, the CRC is preferably not greater than 70 g/g, more preferably not greater than 50 g/g, and further preferably not greater than 40 g/g.

When the above CRC is less than 5 g/g, the amount of absorption is small, and the water-absorbing agent is not suitable as an absorbent body for absorbent articles such as disposable diapers and the like. In addition, when the above CRC exceeds 70 g/g, the speed at which body fluids such as urine, blood, and the like are absorbed decreases, and thus the water-absorbing agent is not suitable for use for high water absorption speed-type disposable diapers and the like. The CRC can be controlled by changing the types and the amounts of the internal crosslinking agent, a surface-crosslinking agent, and the like.

[3-2] Water-Soluble Content (Ext)

The Ext is normally 1 to 40% by mass, preferably 2 to 35% by mass, more preferably 3 to 30% by mass, further preferably 4 to 25% by mass, and particularly preferably 5 to 20% by mass.

When the Ext exceeds the above range, the water-absorbing agent may have low gel strength and inferior water absorption capacity under load and inferior liquid permeability. When the Ext is below the above range, the CRC may be excessively low. In both cases, since the Re-Wet increases, the water-absorbing agent is not suitable as an absorbent body for absorbent articles such as disposable diapers and the like. The Ext can be controlled by changing the types and the amounts of the internal crosslinking agent and the like.

[3-3] Moisture Content

The moisture content of the water-absorbent resin particles (water-absorbing agent) is preferably greater than 0% by mass and not greater than 20% by mass, more preferably 1 to 15% by mass, further preferably 2 to 13% by mass, and particularly preferably 2 to 10% by mass. By making the moisture content to be within the above range, a water-absorbing agent having excellent powder characteristics (e.g., fluidity, transportability, damage resistance, etc.) is obtained.

[3-4] Particle Size

The mass-average particle diameter (D50) of the water-absorbent resin particles (water-absorbing agent) is as described above, and is preferably not less than 200 μm, more preferably 200 to 600 μm, further preferably 250 to 550 μm, and particularly preferably 300 to 500 μm. In addition, the proportion of the particles having a particle diameter of less than 150 μm is preferably not greater than 10% by mass, more preferably not greater than 8% by mass, and further preferably not greater than 6% by mass. Moreover, the proportion of the particles having a particle diameter of greater than 850 μm is preferably not greater than 5% by mass, more preferably not greater than 3% by mass, and further preferably not greater than 1% by mass. The water-absorbing agent includes preferably 90% by mass or greater, more preferably 95% by mass or greater, further preferably 97% by mass or greater, and particularly preferably 99% by mass or greater of particles having a particle diameter of 150 to 850 μm. Ideally, the proportion of the particles having a particle diameter of 150 to 850 μm is 100% by mass. The logarithmic standard deviation (σζ) of the particle size distribution is preferably 0.20 to 0.50, more preferably 0.25 to 0.40, and further preferably 0.27 to 0.35.

[3-5] AAP (Water Absorption Capacity Under Load)

The AAP (water absorption capacity under load) of the water-absorbent resin particles (water-absorbing agent) is preferably not less than 15 g/g, more preferably not less than 20 g/g, further preferably not less than 23 g/g, particularly preferably not less than 24 g/g, and most preferably not less than 25 g/g. The upper limit thereof is not particularly limited, but the AAP is preferably not greater than 30 g/g.

When the above AAP is less than 15 g/g, the amount of liquid return (sometimes referred to as "Re-Wet") when pressure is applied to the absorbent body increases, and thus the water-absorbing agent is not suitable as an absorbent body for absorbent articles such as disposable diapers and the like. The AAP can be controlled by adjustment of the particle size, changing the surface-crosslinking agent, and the like.

[3-6] Vortex (Water Absorption Speed)

The Vortex (water absorption speed) of the water-absorbent resin particles (water-absorbing agent) is preferably not longer than 60 seconds, more preferably not longer than 50 seconds, further preferably not longer than 40 seconds, particularly preferably not longer than 30 seconds, and most preferably not longer than 25 seconds. The lower limit thereof is not particularly limited, but is preferably not shorter than 5 seconds and more preferably not shorter than 10 seconds.

By making the Vortex within the above range, a predetermined amount of liquid can be absorbed in a short time. When the water-absorbing agent is used as an absorbent body for absorbent articles such as disposable diapers and the like, the time when the user feels wet on the skin is reduced and discomfort is less likely to be provided to the user, and the amount of leakage can also be reduced.

[4] Application of Water-Absorbent Resin Particles (Water-Absorbing Agent)

Application of the water-absorbent resin particles (water-absorbing agent) is not particularly limited, and preferable examples thereof include application as an absorbent body for absorbent articles such as disposable diapers, sanitary napkins, incontinence pads, and the like. In particular, the water-absorbing agent can be used as an absorbent body for high-concentration disposable diapers. Furthermore, since the water-absorbing agent has excellent absorption time and a controlled particle size distribution, when the water-absorbing agent is used in an upper layer of the absorbent body, significant effects can be expected.

In addition, as the raw material of the absorbent body, an absorbent material such as pulp fibers and the like can be used together with the water-absorbing agent. In this case, the amount of the water-absorbing agent (core concentration) contained in the absorbent body is preferably 30% by mass to 100% by mass, more preferably 40% by mass to 100% by mass, further preferably 50% by mass to 100% by mass, even more preferably 60% by mass to 100% by mass, particularly preferably 70% by mass to 100% by mass, and most preferably 75% by mass to 95% by mass.

By making the core concentration within the above range, in the case where the absorbent body is used in an upper layer of an absorbent article, the absorbent article can be kept in a white state providing clean feel. Furthermore, the absorbent body is excellent in diffusion property with respect to body fluids such as urine, blood, and the like, and thus an increase in absorption amount can be expected due to efficient liquid distribution.

EXAMPLES

The following will describe the present invention more specifically by means of Experimental Examples. However, the present invention is not limited to the description thereof, and an Experimental Example obtained by appropriately combining technical means that are disclosed in the respective Experimental Examples is also included in the technical scope of the present invention.

The term "water-absorbent resin" described below means a dried polymer that has undergone a drying step, a surface-crosslinked particulate dried polymer, or a particulate dried polymer whose particle size is adjusted after being surface-crosslinked, and the term "hydrous gel" means a crosslinked hydrogel polymer or particulate crosslinked hydrogel polymer that has not undergone a drying step.

Unless specifically noted otherwise, a power source of 60 Hz and 200 V or 100 V was used for electric apparatuses (including an apparatus for measuring physical properties of a water-absorbent resin) used in Experimental Examples. In addition, unless specifically noted otherwise, various physical properties of a water-absorbent resin and a hydrous gel described below were measured under conditions of room temperature (20° C. to 25° C.) and a relative humidity of 50% RH±10%.

Furthermore, for the sake of convenience, "liter" is sometimes represented as "1" or "L", and "% by mass" or "% by weight" is sometimes represented as "wt %". In measurement of a trace component, the detection limit or less is sometimes represented by N. D (Non Detected).

[Methods for Measuring Physical Properties]

(a) CRCs (Centrifuge Retention Capacities) of Water-Absorbent Resin and Hydrous Gel The CRC (centrifuge retention capacity) of a water-absorbent resin was measured according to the EDANA method (ERT441.2-02). In addition, for the CRC (centrifuge retention capacity) of a hydrous gel, the same operations as in the EDANA method (ERT441.2-02) were performed except the mass of a sample was changed to 0.4 g as the hydrous gel and the free swelling time was changed to 24 hours. Furthermore, separately, a solid content rate α of the hydrous gel was measured according to the following (f), and the CRC of the hydrous gel was calculated according to the following (formula 1).

$$\text{CRC of hydrous gel (g/g)} = \{(mwi-mb) - msi \times (\alpha/100)\} / \{msi \times (\alpha/100)\} \quad \text{(formula 1)}$$

In (formula 1), msi is the mass (unit: g) of the hydrous gel before measurement, mb is the mass (unit: g) of a Blank (only an unwoven fabric) after free swelling and dehydration, mwi is the mass (unit: g) of the hydrous gel (including an unwoven fabric) after free swelling and dehydration, and α is the solid content rate (unit: % by mass) of the hydrous gel before measurement.

(b) Exts (Water-Soluble Contents) of Water-Absorbent Resin and Hydrous Gel

The Ext (water-soluble content) of a water-absorbent resin was measured according to the EDANA method (ERT470.2-02). In addition, for the Ext (water-soluble content) of a hydrous gel, the same operations as in the EDANA method (ERT470.2-02) were performed except the mass of a sample was changed to 2.0 g as the hydrous gel. Furthermore, separately, a solid content rate α of the hydrous gel was measured according to the following (f), and the Ext of the hydrous gel was calculated according to the following (formula 2).

$$\text{Ext of hydrous gel (\% by mass)} = \{(VHCl.s - VHCl.b) \times CHCl \times Mw \times Fdil \times 100\} / (ms \times (\alpha/100) \times 1000) \quad \text{(formula 2)}$$

In (formula 2), VHCl.s is the amount of HCl (unit: ml) required to adjust the pH of a filtrate containing a dissolved polymer from pH 10 to pH 2.7, VHCl.b is the amount of HCl (unit: ml) required to adjust the pH of a Blank (a 0.9% by mass sodium chloride aqueous solution) from pH 10 to pH 2.7, CHCl is the concentration of an HCl solution (unit: mole/l), Mw is the average molecular weight (unit: g/mole) of a monomer unit in an acrylic acid (salt) polymer, Fdil is a dilution of the filtrate containing a dissolved polymer, ms is the mass (unit: g) of the hydrous gel before measurement, and a is the solid content rate (unit: % by mass) of the hydrous gel before measurement. For example, when the amount of the filtrate used for titration is 50 g and the amount of a physiological saline solution (0.9% by mass sodium chloride aqueous solution) required for extraction of the water-soluble content is 200 g, the dilution Fdil is calculated as Fdil=50 g/200 g=0.4.

(c) Moisture Content and Solid Content Rate of Water-Absorbent Resin

The moisture content of a water-absorbent resin was measured according to the EDANA method (ERT430.2-02). In the present invention, measurement was taken with its sample amount changed to 1.0 g and its drying temperature changed to 180° C. The solid content rate (% by mass) was obtained by subtracting the moisture content (% by mass) from 100% by mass.

(d) Particle Size of Water-Absorbent Resin

The particle size (particle size distribution, mass-average particle diameter (D50), and logarithmic standard deviation (σζ) of the particle size distribution) of a water-absorbent resin was measured according to the method described in Columns 27 and 28 of U.S. Pat. No. 7,638,570.

(e) Polymerization Ratio and Residual Monomer of Hydrous Gel 1.00 g of a hydrous gel was put into 1000 g of ion-exchanged water, and the mixture was stirred at 300 rpm for 2 hours. Then, the mixture was filtrated to remove insoluble material. The amount of the monomer extracted in the filtrate obtained by the above operation was measured by using liquid chromatography. For the obtained data, correction was performed in terms of gel solid content according to the following (formula 3), a polymerization ratio C (% by mass) of the hydrous gel was obtained, and a residual monomer amount R (% by mass) of the hydrous gel was obtained according to the following (formula 4).

$$C \text{ (\% by mass)} = 100 \times \{1 - m/(\alpha \times M/100)\} \quad \text{(formula 3)}$$

$$R \text{ (\% by mass)} = 100 - C \quad \text{(formula 4)}$$

In (formula 3), M means the mass (g) of the hydrous gel, and a means the solid content rate (% by mass) of the hydrous gel. In (formula 4), C means the polymerization ratio (% by mass) of the hydrous gel. The solid content rate α of the hydrous gel is measured according to the following (f).

(f) Moisture Content and Solid Content Rate of Hydrous Gel

The moisture content of a hydrous gel was measured according to the EDANA method (ERT430.2-02). At the time of measurement, the mass of a sample was changed to 2.0 g, the drying temperature was changed to 180° C., and the drying time was changed to 24 hours. Specifically, 2.0 g of the hydrous gel was put into an aluminum cup having a bottom surface with a diameter of 50 mm, and then the total mass W1 (g) of the sample (the hydrous gel and the aluminum cup) was accurately weighed. Next, the sample was left at rest within an oven whose atmospheric temperature was set to 180° C. After 24 hours elapsed, the sample was taken out of the oven, and the total mass W2 (g) was weighed with precision. When the mass of the hydrous gel subjected to this measurement was denoted by M (g), the moisture content (100−α) of the hydrous gel (% by mass) was obtained according to the following (formula 5). α is the solid content rate (% by mass) of the hydrous gel.

$$(100-\alpha) \text{ (\% by mass)} = \{(W1-W2)/M\} \times 100 \quad \text{(formula 5)}$$

(g) Particle Size of Particulate Hydrous Gel

The particle size (mass-average particle diameter (D50) and logarithmic standard deviation (σζ) of the particle size distribution) of a particulate hydrous gel was measured according to the following method.

20 g of a particulate hydrous gel (solid content rate: α % by mass) with a temperature of 20 to 25° C. was added to 1000 g of a 20% by mass sodium chloride aqueous solution containing 0.08% by mass of sodium polyoxyethylene lauryl sulfate (surfactant) (hereinafter, referred to as "sodium polyoxyethylene lauryl sulfate aqueous solution") to make a dispersion liquid, and the dispersion liquid was stirred with a stirrer tip having a length of 50 mm and a diameter of 7 mm at 300 rpm for 16 hours. The used container is a polypropylene container having a cylindrical column shape (height: 21 cm, diameter: 8 cm, and inner capacity: about 1.14 L).

After the end of the stirring, the dispersion liquid was put into a center portion of JIS standard sieves (diameter: 21 cm, mesh size: 8 mm/4 mm/2 mm/1 mm/0.60 mm/0.30 mm/0.15 mm/0.075 mm) provided on a rotary table. The hydrous gel was classified by repeating, four times, an operation in which the entire hydrous gel was washed onto the sieves using 100 g of the sodium polyoxyethylene lauryl sulfate aqueous solution and then 6000 g of the sodium polyoxyethylene lauryl sulfate aqueous solution was uniformly poured from a height of 30 cm on the upper side using a shower (72 holes, liquid volume: 6.0 [L/min]), such that the pouring range (50 cm$^2$) covered the entire sieves, while rotating the sieves by hand (20 rpm). The classified hydrous gel on the sieve at the first stage was drained for 2 minutes and then weighed. Also for the sieves at the second and subsequent stages, classification was performed by the same operation, and the hydrous gel remaining on each sieve after draining was weighed. The above sieves were changed as appropriate depending on the gel particle diameter. For example, when the particle diameter of a hydrous gel was small and clogging occurred in the sieves having a mesh size of 0.15 mm and 0.075 mm, classification was performed with these sieves replaced with JIS standard sieves having a larger diameter (diameter: 30 cm, mesh size: 0.15 mm, 0.075 mm).

The percentage (% by mass) of the hydrous gel remaining on each sieve was calculated by the following (formula 6) from the mass of the hydrous gel. The mesh size of each sieve after draining was calculated according to the following (formula 7), and the particle size distribution of the hydrous gel was plotted on logarithmic probability paper. The particle diameter at which cumulative sieve % R on the plot corresponds to 50% by mass was defined as the mass-average particle diameter (D50) of the hydrous gel. In addition, a particle diameter corresponding to cumulative sieve % R=84.1% (defined as X1) and a particle diameter corresponding to cumulative sieve % R=15.9% (defined as X2) were obtained from the above plot, and a logarithmic standard deviation (σζ) was obtained by the following (formula 8). A smaller σζ value means a narrower particle size distribution.

$$X(\%) = (w/W) * 100 \quad \text{(formula 6)}$$

$$R(\alpha)(\text{mm}) = (20/W)^{1/3} * r \quad \text{(formula 7)}$$

In (formula 6) and (formula 7),
X: the percentage by mass (%) of the hydrous gel remaining on each sieve after classification and draining
w: the mass (g) of the hydrous gel remaining on each sieve after classification and draining
W: the total mass (g) of the hydrous gels remaining on the respective sieves after classification and draining
R(α): the mesh size (mm) of a sieve in terms of a hydrous gel having a solid content rate α (% by mass)
r: the mesh size (mm) of a sieve with which the cross-linked hydrogel polymer (hydrous gel particles) swollen in the 20% by mass aqueous sodium chloride solution was classified.

$$\sigma\zeta = 0.5 \times \ln(X2/X1) \quad \text{(formula 8)}$$

(h) Mass-Average Particle Diameter (d1) in Terms of Solid Content of Hydrous Gel A mass-average particle diameter in terms of solid content (mass-average particle diameter after drying of hydrous gel particles) d1 was obtained according to the following (formula 9) from the solid content rate (α) of the hydrous gel in the above (f) and the mass-average particle diameter (D50) of the particulate hydrous gel in the above (g).

$$\text{Solid } D50 = \text{Gel } D50 \times (\alpha/100)^{1/3} \quad \text{(formula 9)}$$

In (formula 9),
Gel D50: the mass-average particle diameter (μm) of the hydrous gel particles
α: the solid content rate (% by mass) of the hydrous gel particles
Solid D50: the mass-average particle diameter (μm) in terms of dried material of the hydrous gel particles.

(i) Vortex (Absorption Time) of Water-Absorbent Resin

The Vortex (absorption time) of a water-absorbent resin was measured according to the following procedure. First, 0.02 parts by mass of Food Blue No. 1 (brilliant blue), which is a food additive, was added to 1000 parts by mass of a physiological saline solution (0.9% by mass sodium chloride aqueous solution) prepared beforehand, and then the temperature of the solution was adjusted to 30° C.

Subsequently, 50 ml of the physiological saline solution was weighed in a beaker having a capacity of 100 ml, and 2.0 g of the water-absorbent resin was put into the beaker while stirring the physiological saline solution at 600 rpm with a stirrer tip having a length of 40 mm and a diameter of 8 mm. With the time of input of the water-absorbent resin as a start point, a time taken until the water-absorbent resin absorbed the physiological saline solution and covered the stirrer tip was measured as the Vortex (absorption time) (unit: seconds).

(j) AAP (Water Absorption Capacity Under Load) of Water-Absorbent Resin

The AAP (water absorption capacity under load) of a water-absorbent resin was measured according to the EDANA method (ERT442.2-02). Measurement was taken with its load condition changed to 4.83 kPa (0.7 psi).

Production Example 1

Prepared was a monomer aqueous solution containing 300 parts by mass of acrylic acid, 100 parts by mass of a 48% by mass sodium hydroxide aqueous solution, 0.61 parts by mass of polyethylene glycol diacrylate (average number n: 9), 16.4 parts by mass of a 0.1% by mass trisodium diethylenetriamine pentaacetate aqueous solution, and 273.2 parts by mass of deionized water.

Next, the monomer aqueous solution adjusted to 38° C. was continuously supplied by using a metering pump, and then 150.6 parts by mass of a 48% by mass sodium hydroxide aqueous solution was continuously mixed thereinto by line mixing. At this time, the temperature of the monomer aqueous solution rose to 87° C. due to heat of neutralization.

Furthermore, 14.6 parts by mass of a 4% by mass sodium persulfate aqueous solution was continuously mixed by line mixing, and then the mixture was continuously supplied to a continuous polymerization machine having a flat polymerization belt with weirs at both edges, such that a thickness of the mixture was 10 mm. Thereafter, polymerization was continuously carried out for a polymerization time of 3 minutes to obtain a belt-shaped crosslinked hydrogel polymer (1a). A strip-shaped hydrous gel (1b) having a cut length of 300 mm was obtained by continuously cutting the obtained belt-shaped hydrous gel (1a) in a width direction with respect to the advancement direction of the polymerization belt at regular intervals.

The obtained strip-shaped hydrous gel (1b) was put into a screw extruder, and gel-crushing was performed. As the screw extruder, a meat chopper having a screw shaft outer diameter of 86 mm and provided with a porous plate having a diameter of 100 mm, a pore diameter of 8.0 mm, and a thickness of 10 mm at an end portion, was used. Gel-crushing (first gel-crushing) was performed while supplying water and steam simultaneously with the hydrous gel (1b). Subsequently, the porous plate was replaced by a porous plate having a pore diameter of 4.7 mm, and gel-crushing (second gel-crushing) was further performed on the ground gel obtained by the first gel-crushing, while supplying water and steam. Regarding an obtained particulate hydrous gel (1c), the solid content rate was 44% by mass (the moisture content was 56% by mass), the average particle diameter d1 in terms of solid content was 130 µm, and the proportion of particles having a particle diameter of less than 150 µm was about 53% by mass. In addition, the polymerization ratio of the particulate hydrous gel (1c) was 98.6%, the CRC thereof was 36 g/g, and the water-soluble content thereof was 6%.

The obtained particulate hydrous gel (1c) was dried at 190° C. for 30 minutes using a hot air drying machine, to obtain dried material. The dried material was ground using a roll mill (manufactured by Inokuchi Giken), and then classified with 850 µm and 150 µm JIS standard sieves to obtain a particulate dried polymer (A1). Regarding the particle size distribution of the particulate dried polymer (A1), the proportion of particles that pass through an 850 µm sieve and do not pass through a 600 µm sieve was 3% by mass, the proportion of particles that pass through a 600 µm sieve and do not pass through a 500 µm sieve was 10% by mass, the proportion of particles that pass through a 500 µm sieve and do not pass through a 300 µm sieve was 54% by mass, the proportion of particles that pass through a 300 µm sieve and do not pass through a 150 µm sieve was 31% by mass, and the proportion of particles that pass through a 150 µm sieve and do not pass through a 45 µm sieve was 2% by mass. The mass-average particle diameter (D50) of the particulate dried polymer (A1) was 346 µm, and the σζ thereof was 0.355. The CRC of the particulate dried polymer (A1) was 46.6 g/g, and the moisture content thereof was 4% by mass.

Production Example 2

A strip-shaped hydrous gel (1b) was obtained by performing the same operations as in Production Example 1. Next, the hydrous gel (1b) was put into a screw extruder, and gel-crushing was performed. As the screw extruder, a meat chopper having a screw shaft outer diameter of 86 mm and provided with a porous plate having a diameter of 100 mm, a pore diameter of 9.5 mm, and a thickness of 10 mm at an end portion, was used. Gel-crushing (first gel-crushing) was performed while supplying water and steam simultaneously with the hydrous gel (1b). Regarding an obtained particulate hydrous gel (1d), the solid content rate was 49% by mass (the moisture content was 51% by mass), the average particle diameter d1 in terms of solid content was 2000 µm, and the proportion of particles having a particle diameter of less than 150 µm was about 4.9% by mass. In addition, the polymerization ratio of the particulate hydrous gel (1d) was 98.6%, the CRC thereof was 34 g/g, and the water-soluble content thereof was 4%.

The obtained particulate hydrous gel (1d) was dried at 190° C. for 30 minutes using a hot air drying machine, to obtain dried material. The dried material was ground using a roll mill (manufactured by Inokuchi Giken), and then classified with 850 µm and 150 µm JIS standard sieves to obtain a particulate dried polymer (A2). Regarding the particle size distribution of the particulate dried polymer (A2), the proportion of particles that pass through an 850 µm sieve and do not pass through a 600 µm sieve was 4% by mass, the proportion of particles that pass through a 600 µm sieve and do not pass through a 500 µm sieve was 12% by mass, the proportion of particles that pass through a 500 µm sieve and do not pass through a 300 µm sieve was 49% by mass, the proportion of particles that pass through a 300 µm sieve and do not pass through a 150 µm sieve was 33% by mass, and the proportion of particles that pass through a 150 µm sieve and do not pass through a 45 µm sieve was 2% by mass. The mass-average particle diameter (D50) of the particulate dried polymer (A2) was 346 µm, and the σζ thereof was 0.384. The CRC of the particulate dried polymer (A2) was 49.6 g/g, and the moisture content thereof was 4% by mass.

Example 1

With respect to 100 parts by mass of the particulate dried polymer (A1) at 60° C. obtained in Production Example 1, a surface-crosslinking agent solution containing 0.025 parts by mass of ethylene glycol diglycidyl ether, 0.3 parts by mass of ethylene carbonate, 0.5 parts by mass of propylene glycol, and 2.0 parts by mass of deionized water was spray-mixed using a continuous high-speed stirring drying machine (turbulizer manufactured by HOSOKAWA MICRON CORPORATION) to obtain humidified material (B1).

The obtained humidified material (B1) was heated using a rotary heating device with heating tubes. The rotary heating device includes a cylindrical rotary container (inner capacity: 100 L) having 10 heating tubes extending in the rotation axis direction thereof and two obstructive walls (donut-shaped partition plates each having one circular opening in a center portion thereof, opening ratio: 8%) therein. In addition, rotary heating device has, at a takeout port thereof, a donut-shaped partition plate (also referred to as a discharge weir) having one circular opening in a center portion thereof (opening ratio: 8%).

Initially, the inner surface of the rotary container was heated to a temperature higher than 180° C. in advance by introducing steam having a gauge pressure of 1.8 MPa (temperature: 210° C.) into each heating tube of the rotary heating device, and the outer wall of the rotary container was further heated sufficiently by a trace. Next, the humidified material (B1) was supplied into the rotary heating device at 40 kg/hr, and was continuously heated while rotating the rotary container such that the Froude number Fr was 0.07. The average retention time of the humidified material (B1) was 30 minutes. During the heating, the supplied volume and the discharged volume of carrier gas (air, 140° C.) were adjusted such that the air pressure difference of the interior of the rotary container with respect to the outer air was −20 Pa and the dew point of the discharged air was 80° C. After the heating, the water-absorbent resin discharged from the rotary heating device was forcedly cooled to 80° C. or lower by cold air, to obtain water-absorbent resin particles (C1). When the obtained water-absorbent resin particles (C1) were visually observed, mixing of colored foreign matter was not observed. The physical properties of the water-absorbent resin particles (C1) are shown in Table 1 below.

Example 2

Water-absorbent resin particles (C2) were obtained in the same manner as Example 1, except the surface-crosslinking agent solution was changed so as to contain 0.4 parts by mass of 1,4-butanediol, 0.6 parts by mass of propylene glycol, and 3.0 parts by mass of deionized water. When the obtained water-absorbent resin particles (C2) were visually observed, mixing of colored foreign matter was not observed. The physical properties of the water-absorbent resin particles (C2) are shown in Table 1 below.

Example 3

Water-absorbent resin particles (C3) were obtained in the same manner as Example 1, except the surface-crosslinking agent solution was changed so as to contain 0.025 parts by mass of ethylene glycol diglycidyl ether, 1.0 part by mass of propylene glycol, and 3.0 parts by mass of deionized water, and the inner surface of the rotary container was heated to a temperature higher than 100° C. in advance by introducing steam having a gauge pressure of 0.1 MPa (temperature: 120° C.) into each heating tube of the rotary heating device. When the obtained water-absorbent resin particles (C3) were visually observed, mixing of colored foreign matter was not observed. The physical properties of the water-absorbent resin particles (C3) are shown in Table 1 below.

Example 4

30 g of the water-absorbent resin particles (C1) obtained in Example 1 was put into a mayonnaise bottle having a capacity of 225 mL together with hydrotalcite ($Mg_6Al_2(OH)_{16}CO_3 \cdot 4H_2O$, volume-average particle diameter: 0.5 μm), and mixed by vibrating the bottle for 3 minutes using a paint shaker (manufactured by Toyo Seiki Seisaku-sho, Ltd.), to obtain water-absorbent resin particles (C4). The hydrotalcite was added in an amount of 0.3 parts by mass with respect to 100 parts by mass of the water-absorbent resin particles (C1). When the obtained water-absorbent resin particles (C4) were visually observed, mixing of colored foreign matter was not observed. The physical properties of the water-absorbent resin particles (C4) are shown in Table 1 below.

Example 5

Water-absorbent resin particles (C5) were obtained in the same manner as Example 4, except the hydrotalcite was changed to silica (product name "AEROSIL 200CF", manufactured by Nippon Aerosil Co., Ltd.). When the obtained water-absorbent resin particles (C5) were visually observed, mixing of colored foreign matter was not observed. The physical properties of the water-absorbent resin particles (C5) are shown in Table 1 below.

Example 6

Water-absorbent resin particles (C6) were obtained in the same manner as Example 1, except the particulate dried polymer (A1) was changed to the particulate dried polymer (A2) obtained in Production Example 2. When the obtained water-absorbent resin particles (C6) were visually observed, mixing of colored foreign matter was not observed. The physical properties of the water-absorbent resin particles (C6) are shown in Table 1 below.

Example 7

Humidified material (B2) and water-absorbent resin particles (C7) were obtained in the same manner as Example 2, except the particulate dried polymer (A1) was changed to the particulate dried polymer (A2) obtained in Production Example 2. When the obtained water-absorbent resin particles (C7) were visually observed, mixing of colored foreign matter was not observed. The physical properties of the water-absorbent resin particles (C7) are shown in Table 1 below.

Example 8

Water-absorbent resin particles (C8) were obtained in the same manner as Example 3, except the particulate dried polymer (A1) was changed to the particulate dried polymer (A2) obtained in Production Example 2. When the obtained water-absorbent resin particles (C8) were visually observed, mixing of colored foreign matter was not observed. The physical properties of the water-absorbent resin particles (C8) are shown in
Table 1 below.

Comparative Example 1

Figure 8:
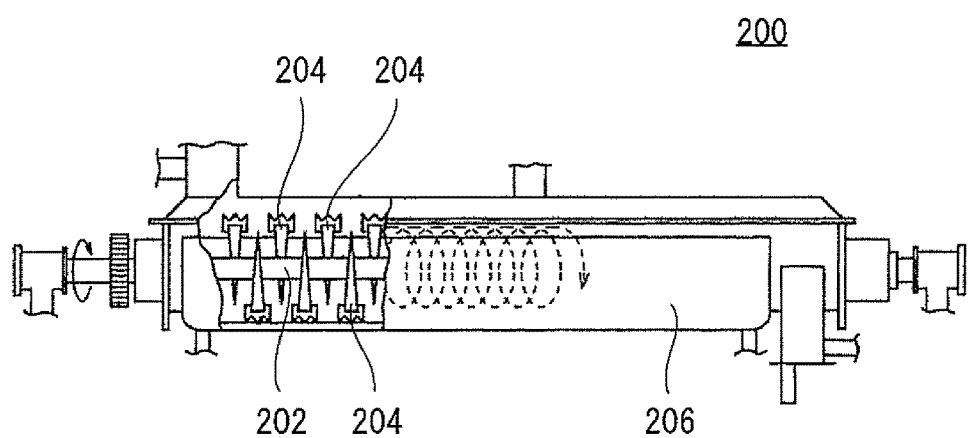
FIG. 8 is a partially cutaway side view showing an example of a drying device (stirring drying machine) used in a conventional production method.

The humidified material (B1) obtained in Example 1 was heated using a conductive heat transfer type groove stirring drying machine (product name "Paddle Dryer NPD-1.6W", manufactured by NARA MACHINERY CO., LTD.) shown in FIG. 8. As shown, the drying machine 200 includes a stirring shaft 202, stirring blades (paddles) 204, and a drum 206. The drying machine 200 had a paddle diameter of 160 mm, a heat transfer area of 2.5 m², and an effective capacity of 0.065 m³.

Initially, a heated heat transfer oil (trade name "Barrel Therm 400", manufactured by Matsumura Oil Co., Ltd.) was introduced into the inner wall, the stirring plates 204, and the rotary shaft 202 of the drying machine 200 to adjust the surface temperatures of the inner wall, the stirring plates 204, and the rotary shaft 202 to 210° C. Heating was performed with an average retention time of 45 minutes at a processing amount of 45 kg/hr, and then forced cooling was performed to 80° C. or lower by cold air, to obtain water-absorbent resin particles (C9). When the obtained water-absorbent resin particles (C9) were visually observed, slight mixing of colored foreign matter was observed. The physical properties of the water-absorbent resin particles (C9) are shown in Table 1 below.

Comparative Example 2

Water-absorbent resin particles (C10) were obtained in the same manner as Comparative Example 1, except the surface-crosslinking agent solution was changed so as to contain 0.025 parts by mass of ethylene glycol diglycidyl ether, 1.0 part by mass of propylene glycol, and 3.0 parts by mass of deionized water, and the surface temperatures of the inner wall, the stirring plates 204, and the rotary shaft 202 of the conductive heat transfer type groove stirring drying machine 200 were changed to 120° C. When the obtained water-absorbent resin particles (C10) were visually observed, slight mixing of colored foreign matter was observed. The physical properties of the water-absorbent resin particles (C10) are shown in Table 1 below.

Comparative Example 3

Water-absorbent resin particles (C11) were obtained in the same manner as Comparative Example 1, except the humidified material (B1) was changed to the humidified material (B2) obtained in Example 7. When the obtained water-absorbent resin particles (C11) were visually observed, slight mixing of colored foreign matter was observed. The physical properties of the water-absorbent resin particles (C11) are shown in Table 1 below.

Comparative Example 4

Water-absorbent resin particles (C12) were obtained in the same manner as Comparative Example 3, except the surface-crosslinking agent solution was changed so as to contain 0.025 parts by mass of ethylene glycol diglycidyl ether, 1.0 part by mass of propylene glycol, and 3.0 parts by mass of deionized water, and the surface temperatures of the inner wall, the stirring plates 204, and the rotary shaft 202 of the conductive heat transfer type groove stirring drying machine 200 were changed to 120° C. When the obtained water-absorbent resin particles (C12) were visually observed, slight mixing of colored foreign matter was observed. The physical properties of the water-absorbent resin particles (C12) are shown in Table 1 below.

TABLE 1

| | Water-absorbent resin particles | 150 μm passing ratio wt. % | Average particle diameter μm | Moisture content wt. % | CRC g/g | AAP g/g |
|---|---|---|---|---|---|---|
| Example 1 | C1 | 2.4 | 345 | 1.5 | 34 | 23 |
| Example 2 | C2 | 2.3 | 350 | 1.7 | 34 | 22 |
| Example 3 | C3 | 2.2 | 353 | 7.0 | 33 | 21 |
| Example 4 | C4 | 2.4 | 345 | 1.5 | 34 | 22 |
| Example 5 | C5 | 2.4 | 345 | 1.5 | 34 | 17 |
| Example 6 | C6 | 2.1 | 346 | 1.5 | 34 | 24 |
| Example 7 | C7 | 2.1 | 348 | 1.7 | 34 | 23 |
| Example 8 | C8 | 2.0 | 355 | 7.0 | 33 | 22 |
| Comparative Example 1 | C9 | 5.0 | 325 | 1.5 | 34 | 21 |
| Comparative Example 2 | C10 | 4.0 | 332 | 7.0 | 33 | 20 |
| Comparative Example 3 | C11 | 2.7 | 342 | 1.7 | 34 | 23 |
| Comparative Example 4 | C12 | 2.5 | 344 | 7.0 | 33 | 21 |

The 150 μm sieve passing ratios and the average particle diameters in the Examples and the Comparative Examples were measured by classification with JIS standard sieves having mesh sizes of 850 μm, 600 μm, 500 μm, 300 μm, and 150 μm.

CONCLUSION (1) From comparison between Examples 1 to 3 and 6 to 8 and Comparative Examples 1 to 4, it is found that water-absorbing agents in which the amount of fine powder is small and colored foreign matter is not mixed and which have excellent fluid retention performance are obtained by surface-crosslinking the particulate dried polymer (A1) and the particulate dried polymer (A2) having a moisture content of not greater than 15 parts by mass using the rotary heating device with heating tubes.

(2) From the results of Examples 4 and 5, it is found that, also in surface treatment of the surface-crosslinked water-absorbent resin particles (C1) having a moisture content of not greater than 15% by mass, an effect that generation of fine powder is inhibited and colored foreign matter is reduced without decreasing predetermined fluid retention performance is obtained by using the rotary heating device with heating tubes.

As described above, in the production method according to the present invention, mechanical and thermal damage to the water-absorbent resin particles was reduced by using a heating device having a specific structure in the surface-crosslinking step, particularly, the heating step. Thus, a water-absorbing agent in which generation of fine powder and a decrease in physical properties were inhibited and colored foreign matter was not mixed was able to be efficiently produced.

INDUSTRIAL APPLICABILITY

The water-absorbent resin particles obtained by the present invention are suitable for application as an absorbent body for sanitary articles such as disposable diapers and the like.

DESCRIPTION OF THE REFERENCE CHARACTERS

100 . . . heating device
4 . . . main portion
6 . . . input portion
8 . . . takeout portion
10 . . . rotary container
11, 11*a*, 11*b* . . . obstructive wall
12 . . . heating tube
14 . . . first gear
16 . . . second gear
18 . . . packing
20 . . . main tube
22 . . . hopper
28 . . . inner space
40 . . . takeout port
44 . . . steam inlet
46 . . . drain
200 . . . stirring drying machine
202 . . . stirring shaft
204 . . . stirring blade
206 . . . drum

The invention claimed is:

1. A method for producing water-absorbent resin particles, the method comprising:
   a surface-crosslinking step of heating a mixture of a surface-crosslinking agent and a particulate dried polymer obtained with an acid group-containing unsaturated monomer as a main component, wherein
   a moisture content of the particulate dried polymer is not greater than 15% by mass, and
   a heating device is used in the surface-crosslinking step, wherein
   the heating device includes a rotary container, a plurality of heating tubes that are located within the rotary container, extend in an axial direction of the rotary container, and rotate together with the rotary container, and at least one obstructive wall provided within the rotary container.

2. The method according to claim 1, wherein a heat medium of 100° C. or higher is supplied to the heating tubes.

3. The method according to claim 1, wherein a temperature of an inner surface of the rotary container is not lower than 100° C.

4. The method according to claim 1, wherein the temperature of the inner surface of the rotary container is set to be not lower than 100° C. before the mixture of the particulate dried polymer and the surface-crosslinking agent is put inside.

5. The method according to claim 1, wherein a gas is introduced into the rotary container, and the temperature of the inner surface of the rotary container is higher than a temperature of the gas.

6. The method according to claim 5, wherein the temperature of the gas to be introduced into the rotary container is not lower than 100° C.

7. The method according to claim 1, further comprising a cooling step of cooling the particulate dried polymer that is surface-crosslinked in the surface-crosslinking step.

8. The method according to claim 1, wherein a temperature of the particulate dried polymer mixed with the surface-crosslinking agent is 30 to 120° C.

9. The method according to claim 1, wherein an average particle diameter of the particulate dried polymer mixed with the surface-crosslinking agent is 200 to 600 μm.

10. The method according to claim 1, wherein a Froude number Fr of the heating device is 0.005 to 0.5.

11. The method according to claim 1, wherein the particulate dried polymer is a crosslinked product containing a poly(meth)acrylic acid (salt) as a main component.

12. A heating device for heating a mixture of a surface-crosslinking agent and a particulate dried polymer obtained with an acid group-containing unsaturated monomer as a main component and having a moisture content of not greater than 15% by mass, the heating device comprising:
    a rotary container;
    a plurality of heating tubes that are located within the rotary container, extend in an axial direction of the rotary container, and rotate together with the rotary container;
    at least one obstructive wall provided within the rotary container; and
    a means for introducing and discharging a gas into and from the rotary container.

13. The heating device according to claim 12, wherein a number of heating tubes is not less than five, and the heating tubes are not in contact with an inner surface of the rotary container in the axial direction.

14. The heating device according to claim 12, further comprising a heating means or a thermal insulating means on an outer peripheral surface of the rotary container.

15. The heating device according to claim 12, wherein the rotary container is inclined from one end thereof toward another end thereof.

16. The heating device according to claim 12, wherein an opening ratio of the obstructive wall is 1 to 90%.

17. The heating device according to claim 12, wherein a ratio of a heat transfer area to an effective capacity of the rotary container (heat transfer area/effective capacity) is not less than 10 $m^{-1}$, and the heat transfer area is a sum of areas of outer peripheral surfaces of the heating tubes and an area of an inner peripheral surface of the rotary container.

18. The heating device according to claim 12, wherein the plurality of heating tubes are arranged radially from a rotation axis of the rotary container toward an outer side in a radial direction so as to be spaced apart from each other.

19. The heating device according to claim 12, wherein the plurality of heating tubes are arranged on two or more concentric circles centered on a rotation axis of the rotary container, so as to be spaced apart from each other.

20. A surface-crosslinking method for heating a mixture of a surface-crosslinking agent and a particulate dried polymer obtained with an acid group-containing unsaturated monomer as a main component, using the heating device according to claim 12, wherein
    a moisture content of the particulate dried polymer to be put into the heating device is not greater than 15% by mass, and
    the surface-crosslinking method comprises introducing a gas as a heat medium into the rotary container to cause a temperature of an inner surface of the rotary container to be not lower than 100° C.

21. The method of claim 1, wherein a plurality of obstructive walls are provided on an inner wall of the rotary container and where the plurality of obstructive walls extend along the inner peripheral surface and are spaced apart in an axial direction of the rotary container.

22. The heating device according to claim 12, wherein the at least one obstructive wall extends along an inner peripheral surface of the rotary container.

23. The heating device according to claim 22, wherein a plurality of obstructive walls are provided so as to be spaced apart from each other in an axial direction of the rotary container.

* * * * *